United States Patent [19]
Carney et al.

[11] 3,997,669
[45] Dec. 14, 1976

[54] TERTIARY AMINOACIDS

[75] Inventors: Richard William James Carney, New Providence; George deStevens, Summit, both of N.J.

[73] Assignee: Ciba-Geigy Corporation, Ardsley, N.Y.

[22] Filed: Feb. 16, 1973

[21] Appl. No.: 333,072

Related U.S. Application Data

[63] Continuation-in-part of Ser. No. 318,158, Dec. 26, 1972, Pat. No. 3,868,391, which is a continuation-in-part of Ser. No. 181,564, Sept. 17, 1971, Pat. No. 3,767,805, which is a continuation-in-part of Ser. No. 40,436, May 25, 1970, abandoned, which is a continuation-in-part of Ser. No. 8,406, Feb. 3, 1970, abandoned, which is a continuation-in-part of Ser. No. 856,154, Sept. 8, 1969, abandoned, which is a continuation-in-part of Ser. No. 843,244, July 18, 1969, Pat. No. 3,641,040, which is a continuation-in-part of Ser. No. 808,343, March 18, 1969, abandoned, which is a continuation-in-part of Ser. No. 790,863, Jan. 13, 1969, abandoned, which is a continuation-in-part of Ser. No. 757,136, Sept. 3, 1968, Pat. No. 3,657,230, which is a continuation-in-part of Ser. No. 716,347, March 27, 1968, abandoned.

[52] U.S. Cl. .................... 424/274; 260/325 PH
[51] Int. Cl.$^2$ ........................... A61K 31/40
[58] Field of Search ............. 424/274; 260/325 PH

*Primary Examiner*—Stanley J. Friedman
*Attorney, Agent, or Firm*—Joseph G. Kolodny; Theodore O. Groeger; John J. Maitner

[57] ABSTRACT

New α-(cyclic tert. aminophenyl)-aliphatic acids, e.g. those of the formula

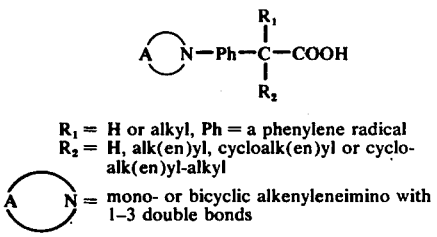

$R_1$ = H or alkyl, Ph = a phenylene radical
$R_2$ = H, alk(en)yl, cycloalk(en)yl or cycloalk(en)yl-alkyl ⌬N = mono- or bicyclic alkenyleneimino with 1–3 double bonds and functional derivatives thereof, are anti-inflammatory agents.

6 Claims, No Drawings

TERTIARY AMINOACIDS

CROSS-REFERENCE TO RELATED APPLICATIONS

This is a continuation-in-part of application Ser. No. 318,158, filed Dec. 26, 1972, (now U.S. Pat. No. 3,868,391), which in turn is a continuation-in-part of application Ser. No. 181,564, filed Sept. 17, 1972, (now U.S. Pat. No. 3,767,805) which in turn is a continuation-in-part of application Ser. No. 40,436, filed May 25, 1970, which in turn is a continuation-in-part of application Ser. No. 8,406, filed Feb. 3, 1970, which in turn is a continuation-in-part of application Ser. No. 856,154, filed Sept. 8, 1969, (all three now abandoned) which in turn is a continuation-in-part of application Ser. No. 843,244, filed July 18, 1969, (now U.S. Pat. No. 3,691,040) which in turn is a continuation-in-part of application Ser. No. 808,343, filed Mar. 18, 1969, which in turn is a continuation-in-part of application Ser. No. 790,863, filed Jan. 13, 1969, (both now abandoned) which in turn is a continuation-in-part of application Ser. No. 757,136, filed Sept. 3, 1968, (now U.S. Pat. No. 3,657,230) which in turn is a continuation-in-part of application Ser. No. 716,347, filed Mar. 27, 1968 (now abandoned).

SUMMARY OF THE INVENTION

The present invention concerns and has for its object the provision of new α-(cyclic tert. aminophenyl)-aliphatic acids, more particularly of those corresponding to Formula I

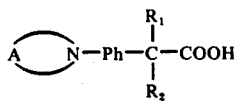

in which $R_1$ is hydrogen or lower alkyl, $R_2$ is hydrogen, lower alkyl, alkenyl, cycloalkyl, cycloalkenyl, cycloalkyl-alkyl or cycloalkenylalkyl, Ph is a phenylene radial and

is a mono- or bicyclic lower alkenyleneimino group containing 1–3 double bonds, or therapeutically acceptable functional acid or amino derivatives thereof, as well as of corresponding pharmaceutical compositions and of methods for the preparation and application of these products. Said compositions are useful antiinflammatory agents in the treatment or management of arthritic and dermatopathologic conditions.

DESCRIPTION OF THE PREFERRED EMBODIMENT

The lower alkyl radicals $R_1$ or $R_2$ represent, for example, methyl, ethyl, n— or i-propyl, —butyl, —pentyl, -hexyl or -heptyl. A lower alkenyl radical $R_2$ is, for example, vinyl, allyl, methallyl, 3-butenyl or 1-pentenyl. The term "lower," referred to above and hereinafter in connection with organic radicals or compounds respectively, defines such with up to 7, preferably up to 4, carbon atoms.

A cycloalkyl or cycloalkenyl radical $R_2$ is preferably 3 to 7 ring-membered and unsubstituted or substituted by up to 4 lower alkyls, such as cyclopropyl, 1- or 2-methyl-cyclopropyl, 1,2-, 2,2- or 2,3-dimethyl-cyclopropyl, 1,2,2- or 1,2,3- trimethylcyclopropyl or 2,2,3,3-tetramethyl-cyclopropyl, cyclobutyl, 3,3-dimethyl-cyclobutyl or 2,2,3-trimethyl-cyclobutyl, cyclopentyl, 2-or 3-methyl-cyclopentyl, 2,5- or 3,4-dimethyl-cyclopentyl, cyclohexyl, 2-, 3- or 4-methyl-cyclohexyl, 2,3-,2,4- or 3,5-dimethylcyclohexyl or 2,4,6-trimethyl-cyclohexyl or cycloheptyl; 2-cyclopropenyl, 2,3-dimethyl-2-cyclopropenyl, 1-, 2- or 3-cyclopentenyl or -cyclohexenyl, 2- or 3-methyl-2-cyclopentenyl, 3,4-dimethyl-3-cyclopentenyl or 2-, 3- or 4-methyl-1 or 2-cyclohexenyl. A cycloalkyl-lower alkyl or cycloalkenyl-lower alkyl radical $R_2$ is one of the above-mentioned lower alkyl groups, preferably such with up to 4 carbon atoms, having in any position thereof, preferably at the terminal carbon atom, one of said cycloalkyl or cycloalkenyl radicals attached, e.g. cyclopropylmethyl, 2-cyclopentylethyl or 3-cyclopentenylmethyl.

The phenylene radical Ph, carrying the tertiary amino group

in the 2-, preferably 3- or especially 4-position, is unsubstituted or substituted in the remaining positions by one or more than one, preferably one or two, of the same or different substituents selected, for example, from lower alkyl, e.g. methyl, ethyl, n- or i-propyl or -butyl, free, etherified or esterified hydroxy or mercapto, such as lower alkoxy or lower alkylmercapto, e.g. methoxy, ethoxy, n- or i-propoxy or -butoxy, methylmercapto or ethylmercapto, halogeno, e.g. fluoro, chloro, bromo or iodo; trifluoromethyl, nitro, amino, preferably di-lower alkylamino or

or lower alkanoylamino, e.g. dimethylamino, N-methyl-N-ethylamino, diethylamino, di-n- or i-propylamino or -butylamino; acetylamino or pivaloylamino, furthermore cyano, carbamoyl, di-lower alkylcarbamoyl, carboxy, lower alkylsulfonyl, sulfo, sulfamoyl or di-lower alkylsulfamoyl, e.g. N,N-dimethylcarbamoyl or -sulfamoyl, methyl- or ethylsulfonyl. More particularly, the phenylene radical Ph especially represents 1,3- or 1,4-phenylene, but also (lower alkyl)-1,3- or 1,4-phenylene, (lower alkoxy)-1,3- or 1,4-phenylene, mono- or di-(halogeno)-1,3- or 1,4-phenylene, (trifluoromethyl)-1,3- or 1,4-phenylene, (nitro)-1,3- or 1,4-phenylene, (amino)-1,3- or 1,4-phenylene, (di-lower alkylamino)-1,3- or 1,4-phenylene or

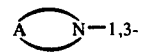

or 1,4-phenylene.

The cyclic tertiary amino group

is preferably a monocyclic 5 to 7 ring-membered lower 2- or 3-alkenyleneimino group or a bicyclic lower alkenyleneimino group containing 5 or 6-membered rings, at most one nitrogen atom in each ring and 1–3 double bonds in the ring not containing the imino nitrogen, e.g. 3-pyrrolino, 3-piperideino, 1,4-pent-2-enyleneimino, 2,5- or 1,6-hex-3-enyleneimino, 2,6- or 1,7-hept-3-enyleneimino; 4,5,6,7-tetrahydroindolino or -isoindolino, 4,7-dihydroindolino or -isoindolino, indolino, isoindolino, 1,2,3,4,5,6,7,8-octahydro-, 1,2,3,4,5,8-hexahydro- or 1,2,3,4-tetrahydroquinolino or -isoquinolino; 1-pyrrolo[2,3-b] pyridyl, 2-pyrrolo[3,4-c]pyridyl or 6-pyrrolo[3,4-b]pyridyl. Said cyclic tert. amino groups may be unsubstituted or substituted, for example, in the aromatic portion as shown for Ph above, and in the aliphatic portion especially by lower alkyl, free, etherified or esterified hydroxy or mercapto, e.g. lower alkoxy, halogeno, lower alkanoyloxy, oxo and/or thiono.

Therapeutically acceptable functional derivatives of the acids of Formula I are preferably their esters, for example, their lower alkyl, lower alkenyl, 3 to 7 ring-membered cycloalkyl, cycloalkenyl, cycloalkyl-lower alkyl or cycloalkenyl-lower alkyl, aryl or aralkyl esters, e.g. the HPh or HPh-lower alkyl esters, free of etherified hydroxy-lower alkyl, e.g. lower alkoxy- or 3 to 7 ring-membered cycloalkoxy-lower alkyl or tert. amino-lower alkyl esters, of which the esterifying moiety has been exemplified above and if it contains hetero atoms, these are separated from each other and the carboxy oxygen by at least 2, preferably 2 or 3 carbon atoms. A tertiary amino group therein is, for example, di-lower alkylamino or lower alkyleneimino, e.g. dimethylamino, diethylamino, pyrrolidino or piperidino, or monoaza-, monooxa- or monothia-lower alkyleneimino, such as piperazino, 4-lower alkylpiperazino, e.g. 4-(methyl or ethyl)-piperazino, morpholino or thiamorpholino. Other functional derivatives of the acids of Formula I are, for example, unsubstituted or substituted amides or thioamides, e.g. mono- or di-lower alkylamides, HPh-amides, HPh-lower alkylamides, monocyclic lower alkyleneamides, monoaza-, or monooxa- or monothialower alkyleneamides, furthermore the corresponding thioamides, hydroxamic acids, nitriles, ammonium or metal salts. Amino derivatives are the N-oxide, lower alkyl- or HPh-lower alkyl quaternaries and acid addition salts.

The compounds of the invention possess valuable pharmacological properties. Besides analgesic and antifungal activity, they exhibit anti-inflammatory effects, as can be demonstrated in in vitro or animal tests, using for the latter advantageously mammals, such as mice, rats or guinea pigs as test objects. The former tests can be performed according to the gradient plate method with fungi selected, for example, from Trichophyton, Microsporum or Epidermophyton, e.g. T. mentagrophytes, T. rubrum or T. sinii, M. canis or M. gypseum; or E. floccosum. The antifungal activity can also be observed in vivo, e.g., according to Molinas, J. Investig. Dermatol. 25, 33(1955), where guinea pigs are infected on the shaven back with a homogenous agar suspension of a 10 day old culture of T. mentagrophytes grown on Sabouraud's agar. Treatment with 0.5–2 percent medicated solutions or ointments is started after 24 hours and continued once daily for 10 days. During this time, portions of hair and skin skales are taken from 5 different sites of the infected area and subcultured on Mycosel agar plates, which are incubated and examined for growth. The analgesic effects can be demonstrated, for example, according to the mouse writhing test, described inter alia by Siegmund et al. Proc. Soc. Exp. Biol. & Med. 95, 729 (1957) at oral doses between about 50 and 200 mg/kg/day. Anti-inflammatory activity can be shown, for example, according to Winter et al, Proc. Soc. Exp. Biol. & Med. 111, 544 (1962). There, the compounds of the invention are applied, in the form of aqueous solutions or suspensions, which may contain carboxymethylcellulose or polyethylene glycol as solubilizers, by stomach tube to male and female mature rats, in the dosage range between about 0.1 and 75 mg/kg/day, preferably between about 0.5 and 50 mg/kg/day, advantageously between about 1 and 25 mg/kg/day. About 1 hour later 0.06 ml of a 1 percent saline suspension of carrageenin is injected into the rat's left hind paw and 3–4 hours subsequently any anti-inflammatory activity can be expressed by the difference of the volume and/or weight of the edematous left paw and that of the right paw, as compared with said difference estimated from untreated control animals. According to the adjuvant arthritis test male rats are sensitized with 0.05 ml of said 1 percent carrageenin suspension, applied under ether anesthesia to all four paws. After 24 hours 0.1 ml of a 1 percent suspension of M. butyricum in mineral oil is injected intradermally into the tail and 7 days later the compounds of the invention are applied as shown above for a 14 day period. The rats are weighed once weekly and the secondary arthritis lesions scored 3 times a week as to number and severity. The results obtained are compared with those of untreated arthritic rats. In view of the test results obtained, the compounds of the invention are useful analgesic, antifungal and especially antiinflammatory agents in the treatment of management of arthritic and dermatopathologic conditions. They are also useful intermediates in the preparation of other valuable products, preferably or phramacologically active compounds.

Preferred compounds of the invention are those of Formula I in which:
a. $R_1$ hydrogen or lower alkyl, $R_2$ is hydrogen, lower alkyl or lower alkenyl, Ph is unsubstituted phenylene or phenylene substituted by one or two members selected from the group consisting of lower alkyl, hydroxy, mercapto, lower alkoxy, lower alkylmercapto, halogeno, trifluoromethyl, nitro, amino, di-lower alkylamino,

lower alkanoylamino, cyano, carbamoyl, dilower alkylcarbamoyl, carboxy, lower alkylsulfonyl, sulfo, sulfamoyl or di-lower alkyl-sulfamoyl, and the group

is monocyclic 5 to 7 ring-membered lower 2- or 3-alkenyleneimino or bicyclic alkenyleneimino containing 5 or 6-membered rings, at most one nitrogen atom in each ring and 1–3 double bonds in the ring not containing the imino nitrogen, which imino groups are unsubstituted or substituted by one or two oxo groups at the carbon atoms adjacent to the imino nitrogen;
b. $R_1$, Ph and

have the meaning given under item a) and $R_2$ is 3 to 7 ring-membered cycloalkyl, cycloalkenyl, cycloalkyl-lower alkyl or cycloalkenyl-lower alkyl, or a lower alkyl ester, lower alkenyl ester, 3 to 7 ring-membered cycloalkyl ester, cycloalkenyl ester, cycloalkyl-lower alkyl ester, cycloalkenyllower alkyl ester, HPh-ester, HPh-lower alkyl ester, hydroxylower alkyl ester, lower alkoxy-lower alkyl ester, di-lower alkylamino-lower alkyl ester, lower alkyleneimino-lower akyl ester, monoaza-, -oxa- or -thia-lower alkyleneimino-lower alkyl ester or

lower alkyl ester in which esters 2 hetero atoms are separated from each other by at least 2 carbon atoms, the amide, thioamide, a mono- or di-lower alkylamide, mono- or dilower alkyl-thioamide, lower alkyleneamide, lower alkylenethioamide, HPh-amide, HPh-thioamide, HPh-lower alkylamide, HPh-lower alkylthioamide, morpholide, thiamorpholide or hydroxamic acid, the N-oxide, a lower alkyl quaternary, HPh-lower alkyl quaternary or a therapeutically useful salt of the compounds listed under items a) or b).

Particularly useful are the compounds of Formula I, in which:
c. $R_1$ is hydrogen, $R_2$ is hydrogen or lower alkyl, Ph is 1,3- or 1,4-phenylene, (lower alkyl1,3- or 1,4-phenylene, (lower alkoxy)-1,3- or 1,4-phenylene, mono- or di-(halogeno)- 1,3- or 1,4-phenylene, (trifluoromethyl)-1,3- or 1,4-phenylene, (nitro)-1,3- or 1,4-phenylene, (amino)-1,3- or 1,4-phenylene, (di-lower alkylamino-1,3- or 1,4-phenylene or

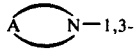

or 1,4-phenylene, the group

is monocyclic 5 to 7 ring-membered lower 2-or 3-alkenyleneimino or bicyclic alkenyleneimino containing only one nitrogen atom, 5 or 6-membered rings and 1-3 double bonds in the isocyclic ring, or said alkenyleneimino radicals containing one or two oxo groups attached to the carbon atoms adjacent to the nitrogen atom;
d. $R_1$, Ph and

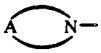

have the meaning under item c) and $R_2$ is 3 to 7 ring-membered cycloalkyl or cycloalkyl-lower alkyl, or a lower alkyl ester, the amide, a mono- or di-lower alkylamide, the N-oxide, an alkali metal or alkaline earth metal salt or a therapeutically useful acid addition salt of the compounds listed under item c) and d).

Outstanding are the compounds of Formula II

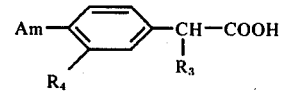

in which:
e. $R_3$ is hydrogen or alkyl with up to 4 carbon atoms, $R_4$ is hydrogen, alkyl or alkoxy with up to 4 carbon atoms, halogeno, trifluoromethyl, nitro, or amino, and Am is 3-pyrrolino, 3-piperideino, 1,6-hex-3-enyleneimino indolino, isoindolino or 1,2,3,4-tetrahydroquinolino or -isoquinolino, or said radicals containing one or two oxo groups attached to the carbon atoms adjacent to the nitrogen atom;
f. $R_4$ and Am have the meaning given under item e) and $R_3$ is 3 or 4 ring-membered lower cycloalkyl or cycloalkylmethyl, or the methyl, ethyl, n- or i-propyl or -butyl ester, the N-oxide, sodium or potassium salt or a therapeutically useful acid addition salt of the compounds listed under items e) and f).

Especially valuable are compounds of the Formula II, in which:
g. $R_3$ is hydrogen, methyl, ethyl, n- or i-propyl, $R_4$ is hydrogen, fluoro, chloro or trifluoromethyl and Am is 3-pyrrolino, 3-piperideino, 2-oxo-3-pyrrolino, maleinimino, isoindolino, 1-oxoindolino, phthalimino or homophthalimino;
h. $R_4$ and Am have the meaning given under item g) and $R_3$ is cyclopropyl or cyclopropylmethyl, the methyl or ethyl ester, the N-oxide, sodium or potassium salt or a therapeutically useful acid addition salt of the compounds listed under items g) and h).

The most preferred embodiments of the present invention are the α-(3-chloro-4-pyrrolinophenyl)-propionic acid, the methyl or ethyl ester, the N-oxide, sodium or potassium salt or a therapeutically useful acid addition salt thereof, which exhibit in the above-described test systems at doses between about 1 and 25 mg/kg/day a high order of anti-inflammatory activity.

The compounds of this invention are prepared according to methods known per se. For example, they are obtained by:
a. converting in a compound of the Formula III

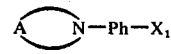

in which $X_1$ is a substituent capable of being converted into the free or functionally converted

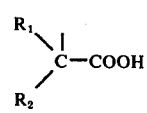

moiety, $X_1$ into said acid group or
b. converting in a compound of Formula IV

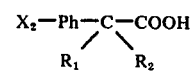

or a functional derivative thereof, in which $X_2$ is a substituent capable of being converted into

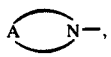

$X_2$ into said cyclic tert. amino group and, if desired, converting any resulting compound into another compound of the invention.

According to process a), the compounds of the invention are prepared either by α) introduction of the whole free or functionally converted acid moiety

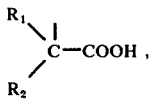

or any part thereof (preferably the carboxylic function), into compounds of Formula III, or by β) liberation of said acid moiety from a suitable group containing already the requied number of carbon atoms, i.e. the liberation of a potential carboxy or alkylidene moiety.

Accordingly, the simplest substituent $X_1$ is a hydrogen atom, a metallic group or a reactively esterified hydroxy group. The former is, for example, an alkali metal, e.g. a lithium atom, or a substituted alkaline earth metal, zinc or cadmium atom, such as halomagnesium or lower alkyl zinc or cadmium, e.g. chloro-, bromo- or iodomagnesium, methyl or ethyl zinc or cadmium. A reactively esterified hydroxy group is preferably such derived from a strong mineral or sulfonic acid, such as a hydrohalic, sulfuric, lower alkane or benzene sulfonic acid, e.g. hydrochloric, hydrobromic, methane-, ethane-, benzene- or p-toluenesulfonic acid. The corresponding starting material of Formula III is reacted with the acid having the formula

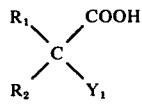

or a suitable derivative, e.g. a corresponding salt, ester, amide or nitrile thereof, in which formulae one of $X_1$ and $Y_1$ is the above-described metallic group and the other said reactively esterified hydroxy group, or $X_1$ is hydrogen and $Y_1$ is a free or reactively esterified hydroxy group. Such reaction is performed according to the classical Grignard or Friedel-Crafts syntheses, in which a new carbon-carbon bond is formed from separate reactants. The latter synthesis is performed in the presence of a Lewis acid, such as an aluminum, boron, antimony V, ferric or zinc salt, e.g. the chlorides thereof, or hydrofluoric, sulfuric or preferably polyphoshoric acid, which latter agent is advantageously used with the above glycolic acids or their derivatives, i.e those in which $Y_1$ is hydroxy. In case $X_1$ is a hydrogen atom and Ph contains a free or functionally converted γ-carboxy-2-alkenyloxy group in the ortho or para position thereto, such allyl ether starting material, e.g. that of the formula

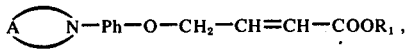

can be rearranged according to the Claisen (Cope) rearrangement procedure, for example, by heating it up to about 300° or less, to yield compounds of Formula I in which $R_2$ is lower alkenyl and Ph contains a hydroxy group ortho or para to the acid moiety, or functional acid derivatives, e.g. esters or lactones, thereof.

The substituent $X_1$ in Formula III is also the group

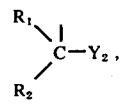

in which $Y_2$ is a metallic group, e.g. such mentioned above, an ammonium group, such as tri-lower alkylammonium or dilower alkyl-aralkylammonium, e.g. trimethylammonium or dimethylbenzylammonium, or a free or reactively converted, such as esterified, etherified or salified, hydroxy group, e.g. such esterified as mentioned above, or etherified with a lower alkanol or aralkanol, or salified with an alkali or alkaline earth metal, e.g. sodium, potassium or calcium. Such metal compound, ester, ether or alcoholate of Formula III is reacted with a reactive derivative of carbonic or formic acid, whereby both reactants at most contain one metal atom. The metal or Grignard compound can be reacted with any suitable, metal free carbonic or formic acid derivative, advantageously carbon dioxide or disulfide, but also a corresponding carbonate or haloformate, e.g diethyl carbonate or thiocarbonate; ethyl or propyl orthocarbonate; ethyl, tert. butyl, allyl, 2-methoxyethyl, 3-chloropropyl, phenyl or benzyl chloroformate; cyanogen or carbamoyl halides, e.g. cyanogen bromide or diethylcarbamoyl chloride. The starting material, in which $Y_2$ is an ammonium or free or reactively converted hydroxy group, is advantageously reacted with a metal cyanide, e.g. sodium or potassium cyanide, and that in which $Y_2$ is free, esterified or salified hydroxy, or the dehydrated unsaturated derivative thereof (wherein $X_1$ is a corresponding 1-alkenyl group) can also be reacted with carbon monoxide. The latter may be applied under neutral, basic or acidic conditions respectively, e.g. in the presence of sulfuric acid, under high pressure and/or temperature, e.g. up to 400° at and 300°, advantageously in the presence of heavy metal catalysts, e.g. nickel or cobalt salts or carbonyl derivatives thereof. The carbon monoxide may also be generated from appropriate sources, such as formic acid and high boiling mineral acids, e.g. sulfuric or phoshoric acid.

Another substituent $X_1$ is the group

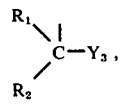

wherein $Y_3$ is a substituent convertible into a free or functionally converted carboxy group. The conversion of $Y_3$ into the latter group can be performed either by oxidation or rearrangement. In the former case $Y_3$ is, for example, methyl, hydroxymethyl, borylmethyl, hydroxyiminomethyl, formyl, lower 1-alkenyl or 1-alkynyl, lower 1,2-dihydroxyalkyl or acyl, such as lower alkanoyl, alkenoyl, free or esterified carboxycarbonyl. In the corresponding starting material of Formula III, containing said potential carboxy function, $Y_3$ is transformed into free or functionally converted carboxy according to standard oxidation methods, for example, with the use of air or pure oxygen, preferably in the presence of catalysts, such as silver, manganese, iron or cobalt catalyst, or with oxidation agents, e.g. hydrogen peroxide or nitric oxides, oxidizing acids or their salts, such as hypohalous, periodic, nitric or percarboxylic acids or suitable salts thereof, e.g. sodium hypochlorite or periodate, peracetic, pergenzoic or monoperphthalic acid, heavy metal salts or oxides, such as alkali metal chromates or permanganates; chromic or cupric salts, e.g. halides or sulfates thereof, or silver, mercuric, vanadium V, chromium VI or manganese IV oxide, in acidic or alkaline media respectively. In said oxidations, for which starting materials are chosen, in which

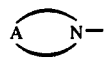

is less sensitive to oxidation than $Y_3$, e.g. bicyclic alkenyleneimino, usually the free carboxylic acids of Formula I, or salts thereof, are obtained. However, by subjecting, for example, a hydroxyiminomethyl compound (oxime) to Beckmann rearrangement, e.g. treatment with sulfuric acid, p-toluenesulfonyl chloride or phosphorus pentachloride, or to oxidation, e.g. with hydrogen peroxide or any of said percarboxylic acids, or reacting the corresponding formyl or acyl compound (aldehyde or ketone) with hydrazoic acid according to the Schmidt reaction, e.g. in the presence of sulfuric acid, or the aldehyde with a sulfonyl- or nitro-hydroxamate, or nitrile, amide or hydroxamic acid will be formed respectively. A starting material in which $Y_3$ is free or esterified carboxycarbonyl, e.g. lower carbalkoxycarbonyl, can be converted into the acid of Formula I either by oxidation, e.g., with hydrogen peroxide in acidic media, such as mineral acids, or by decarbonylation, which preferably is carried out by pyrolysis, advantageously in the presence of copper or glass powder.

Finally, the substituent $X_1$ in Formula III may be such a moiety, which primarily is capable of liberating the required alkylidene group

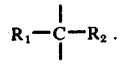

Such moiety is, for example, the free or functionally converted group

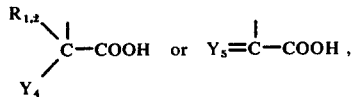

wherein each of $Y_4$ or $Y_5$ are convertible into $R_1$ and/or $R_2$ respectively, for example, by reduction, decarboxylation, deacylation or desulfurization. For example, $Y_4$ is a free or reactively esterified or etherified hydroxy or mercapto group as mentioned above, e.g. hydroxy, mercapto, chloro, bromo, iodo, benzyloxy or benzylmercapto and $Y_5$ a lower alkylidene, cycloalkylidene, cycloalkyl-alkylidene, oxo or thiono group. The corresponding starting material, or the quaternary o- or p-quinonmethides thereof, obtainable by splitting off $Y_4H$ from said compounds of Formula III, in which at least one of $R_1$ and $R_2$ is hydrogen, e.g. with the use of strong mineral acids or alkalis, can be reduced either with catalytically activated or nascent hydrogen, such as hydrogen in the presence of nickel, palladium or platinum catalysts, or with hydrogen generated by electrolysis or the action of metals on acids, alkalis or alcohols, such as zinc, amalgamated zinc, iron or tin on aqueous mineral or carboxylic acids, e.g. hydrochloric or acetic acid, zinc or aluminum-nickel alloys on aqueous alkali metal hydroxides, or sodium, potassium or their amalgams on lower alkanols. Also reducing and/or desulfurizing agents may be applied, depending on the starting material chosen. In case $Y_4$ is hydroxy, the reducing agent may be an aqueous suspension of phosphorus and iodine, hydriodic acid, stannous chloride or sodium sulfite or dithionite, or in case $Y_4$ is esterified hydroxy, e.g. halogeno, an aliphatic or cycloaliphatic metal compound, e.g. a corresponding $R_1$ or $R_2$ lithium or Grignard compound may be used as reducing agent. The latter metal compounds may also be applied in the reduction of said quinonmethides. In case $Y_5$ is oxo, the Clemmensen, Wolff-Kishner or Huang-Minlon procedures may be applied, wherein nascent hydrogen or hydrazine are used, the latter advantageously in the presence of strong alkalis, e.g. high boiling aqueous or glycolic sodium or potassium hydroxide solutions. In the reduction of mercapto, free or ketalized thiono compounds, desulfurization agents are advantageously applied, such as mercury or copper oxide or Raney nickel. In case $Y_4$ represents carboxy, the corresponding malonic acid derivative is decarboxylated by pyrolysis, advantageously in acidic media, or $Y_4$ stands for another acyl radical, such as lower alkanoyl or aralkanoyl, e.g. acetyl or benzoyl, the β-keto acid is subjected to acid splitting by the action of strong alkalis, e.g. those mentioned above.

Another substituent $X_1$, also providing said alkylidene group, is an unsubstituted or substituted acetyl group, e.g. —CO-(CN$_2$)—$R_2$ or CO—(CR$_1$,R$_2$)—halogen. The corresponding unsubstituted acetyl starting material is converted into the compounds of the invention according to the Willgerodt-Kindler reaction, e.g. by the action of sulfur in the presence of ammonia, primary or secondary amines and advantageously of sulfonic acids, e.g. p-toluenesulfonic acid, and said substituted acetyl compounds according to the Wolff (Arndt-Eistert) reaction, e.g. by hydrolysis, alcoholysis, ammonolysis or aminolysis of corresponding α-diazo-ketones, advantageously while irradiated or heated in the presence of copper or silver catalysts, or according to the Favorskii (Wallach) reaction respectively, e.g. by the action of strong alkalis or soluble silver salts, such as silver nitrate, on corresponding α-haloketones.

According to process b), the cyclic tertiary amino group

is either α) introduced into the phenylene moiety Ph, or β) a primary, secondary, acyclic (open) or saturated cyclic tertiary amino group, present therein, converted into the desired unsaturated cyclic tertiary amino group. Accordingly, $X_2$ is, for example, a hydrogen atom, a metallic group or a free or reactively esterified hydroxy group, e.g. those groups shown above, preferably an alkali metal or halogen atom respectively. The corresponding starting material of Formula IV is reacted with the compound

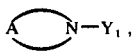

in which one of $X_2$ and $Y_1$ is hydrogen or said metallic group, e.g. lithium or sodium, and the other said free or reactively esterified hydroxy group, e.g. fluorine or chlorine. In case $X_2$ is hydrogen and $Y_1$ halogen, the reaction is carried out analogous to the Friedel-Crafts syntheses mentioned above, i.e. in the presence of Lewis acids or, in case $Y_1$ is hydroxy, in the presence of alkalis, e.g. potassium hydroxide. In case $X_2$ is hydroxy or lower alkanoyloxy, the reaction is advantageously carried out in the presence of a dehydration or dehydrogenation catalyst, such as a mineral acid or a salt thereof, e.g. hydrochloric acid, ammonium sulfite or sodium bisulfite, activated aluminum oxide, Raney nickel or palladium-charcoal.

The conversion of any primary, secondary, acyclic or saturated cyclic tertiary amino group $X_2$ into

can simply be performed by transamination with the amine

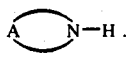

The latter is advantageously used in excess and in the presence or absence of catalysts, e.g. the above-mentioned dehydration of dehydrogenation catalysts, and elevated temperature and/or pressure. A starting material of Formula IV, in which $X_2$ is primary amino, can also be reacted with the glycol, glycolic acid or dicarboxylic acid HO-A-OH, or advantageously a reactive functional derivative thereof, such as an ester, cyclic ether or the dehydrated, unsaturated (olefinic) derivative of said glycol or glycolic acid and/or a halide, anhydride or lactone of the acid, e.g. such mentioned above. These condensations are advantageously carried out in the presence of water or acid binding agents, such as alkali metals, their alcoholates or carbonates and the addition of the unsaturated compounds to the amino group preferably in the presence of catalysts, e.g. copper, cobalt or molybdenum catalysts, and/or acids or bases. A saturated cyclic tert. amino group $X_2$ can be converted into the unsaturated

group, for example, by dehydration, dehydrosulfidation or desamination of a mono- or bicyclic (hydroxy, mercapto, amino, ammonium, hydrazino or hdrazono)-alkyleneimino group, or reactive derivatives thereof, such as a reactive ether or ester of the hydroxy or mercapto compounds, or an acyl derivative of the nitrogen bases, e.g. a tert. butyl ether or a tosylate, brosylate or xanthate respectively. Dehydration is preferably carried out with the use of concentrated mineral or sulfonic acids, Lewis acids or carboxylic acid anhydrides, e.g. hydrobromic, sulfuric, phosphoric or p-toluenesulfonic acid or acetic anhydride. Dehydrosulfidation may be carried out with the use of heavy metal oxides, e.g. mercury or lead oxide and desamination by thermal decomposition of ammonium salts. Preferably reactive esters of the hydroxy compounds or acyl derivatives of the hydrazones are pyrolyzed, advantageously under reduced pressure.

The compounds of the invention so obtained can be converted into each other according to methods known per se. For example, resulting free acids may be esterified with the corresponding alcohols in the presence of a strong acid, e.g. hydrochloric, sulfuric, benzene or p-toluene sulfonic acid, or with diazo compounds, or converted into their halides by treatment with thionyl halides or phosphorus halides or oxyhalides. Resulting esters may be hydrolyzed or transesterified in the presence of acidic or alkaline agents, e.g. mineral or complex heavy metal acids or alkali metal carbonates or alcoholates, or treated with ammonia or corresponding amines. Resulting acid halides may be treated with alcohols, ammonia or amines in order to obtain the corresponding esters or amides respectively. Resulting amides or thioamides (Willgerodt) can be hydrolyzed under acidic or alkaline conditions, e.g. with the use of aqueous mineral and/or carboxylic acids or alkali metal hydroxides, also alcoholyzed, transaminated or desulfurized, e.g. with the use of mercuric oxide or alkyl halides followed by hydrolysis, or oxo compounds sulfurized, e.g. with phosphorus pentasulfide. Resulting compounds which do not contain an oxo group in the bicyclic

moiety can be oxidized therein already with oxygen or other mild oxidation agents, e.g. those mentioned above, to introduce an oxo group into the A-radical thereof, preferably into one or both of the positions adjacent to the imino nitrogen, thus converting the cyclic tertiary amines into lactames or imides respectively. Resulting nitriles likewise can be hydrolyzed or alcoholyzed, e.g. with the use of concentrated aqueous or alcoholic acids or alkalis or also with alkaline hydrogen peroxide. A resulting ester, salt or nitrile, containing in $\alpha$-position at least one hydrogen atom, can be metallized therein, e.g. with the use of alkali metals or their derivatives, such as phenyl lithium, triphenylmethylsodium or sodium hydride, amides or alcoholates, and thereupon reacted with reactive esters of $R_1$—OH and/or $R_2$—OH. Resulting compounds may also be halogenated in the Ph-moiety, e.g. with the use of halogens, which are advantageously applied in the presence of Lewis acids, e.g. ferric, aluminum, antimony III or tin IV halides, or with the use of halogenation agents, e.g. hydrochloric acid and hydrogen peroxide or sodium chlorate, nitrosyl chloride or bromide, bromosuccin- or phthalimide. Furthermore, nitration may be applied to final products, advantageously with the use of nitric acid or nitrates under acidic conditions, e.g. in the presence of sulfuric or trifluoroacetic acid respectively. Resulting nitro compounds may be reduced, for example, with catalytically activated or nascent hydrogen and, if desired, the primary amino compounds obtained, either treated with reactive esters of corresponding alcohols or glycols, or with reactive functional acid derivatives, in order to obtain secondary, tertiary, quaternary or acylated amino compounds respectively. Said prim. amines can also be treated with nitrous acid, to yield diazonium salts, which can be converted according to the Sandmeyer reaction into the corresponding hydroxy, halogeno, cyano, alkoxy or alkylmercapto compounds, e.g. by hydrolyzing the diazonium salt at elevated temperatures, or reacting it with cuprous halides or cyanide or with a lower alkanol or alkylmercaptan respectively, preferably under neutral or slightly acidic or alkaline conditions. In resulting phenolic products, the hydroxy or mercapto group can be etherified, e.g. by reacting the corresponding alkali metal phenolates with lower alkyl halides or sulfonates, or resulting phenol ethers are hydrolyzed, e.g. with the use of strong acids or acidic salts, e.g. hydrobromic acetic acid or pyridine hydrochloride, and aliphatic hydroxy compounds can be dehydrated as shown above. In the above reductions, care should be taken or starting materials and final products properly selected, in order to retain unsaturation in

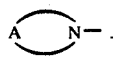

A resulting acid can be converted into its salts according to conventional methods, for example, by reacting it with an about stoichiometric amount of a suitable salt-forming reagent, such as ammonia, an amine or an alkali or alkaline earth metal hydroxide, carbonate or hydrogen carbonate. A salt of this type can be reconverted into the free acid by treatment with an acid, e.g. hydrochloric, sulfuric or acetic acid, until the proper pH has been reached. A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicylic, embonic, nicotinic, methanesulfonic, ethanesulfonic, hydroxy-ethanesulfonic, ethylenesulfonic, benzenesulfonic, halogenbenzenesulfonic, toluensulfonic, naphthalenesulfonic and sulfanilic acid; methionine, tryptophan, lysine and arginine.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The resulting mixtures of isomers can be separated into the single isomers by methods in themselves known, e.g. by fractional distillation, crystallization and/or chromatography. Racemic products can likewise be resolved into the optical antipodes, for example by separation of diastereomeric salts thereof, e.g. by the fractional crystallization of d- or l-tartrates or d-α-(1-naphthyl)ethylamine or 1-cinchonidine salts.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. For example, in most of the above-described oxidation methods, wherein $Y_3$ is converted into a free or functionally converted carboxy group, the corresponding aldehydes ($Y_3$ is formyl) are formed intermediarily. According to the haloform reaction ($Y_3$ is acetyl) intermediarily formed trihaloketones are hydrolyzed under the applied alkaline conditions, to yield the corresponding salts or esters of the acids of Formula I. Also, the quaternary o— or p—quinonmetides may be formed intermediarily from the corresponding starting material in which $Y_4$ is free or reactively esterified hydroxy, e.g. under strongly acidic or alkaline conditions, or during the reduction of compounds in which $Y_5$ is oxo or thiono. The α-diazoketones are usually formed, according to Arndt-Eistert, from the corresponding benzoic acid halides and aliphatic or cycloaliphatic ($R_2$) diazo compounds, whereupon the above-described Wolff rearrangement is performed. Moreover, in the formation of the cyclic tert. amino group

several intermediates are formed from the various starting materials mentioned above. For example, in the reaction of compounds of Formula IV, in which $X_2$ is primary amino, with those of the formula HO—A—OH or its reactive functional derivatives, usually secondary amines or amides are formed, wherein $X_2$ is -NH—A—OH, or reactive amino derivatives of such intermediates. In the process of the invention, those starting materials are advantageously selected, which yield the above-described preferred embodiments of the invention, especially those corresponding to Formula II.

The starting material used is known or, if new, may be prepared according to the methods described for known analogs thereof. For example, compounds of Formula III can be prepared analogous to the process mentioned under item b), i.e. by introduction or construction of the cyclic amino group

In case $X_1$ is a reactively esterified hydroxy group, it may also be introduced either by halogenation, or nitration followed by reduction, diazotization and Sandmeyer reaction. The resulting starting material may be subsequently converted into the metallic compounds, e.g. by reaction with alkali or alkaline earth metals, such as lithium or magnesium, or with dialkyl zinc or cadmium. The allyl ethers for the Claisen rearrangement can be prepared analogous to those described in J. Chem. Soc. 4210 (1963).

The starting material in which $Y_2$ is a metallic group may be prepared as shown above, i.e. by reacting reactive esters of the corresponding benzylalcohols with alkali or alkaline earth metals or dialkyl zinc or cadmium. Otherwise, according to Friedel-Crafts, easily obtainable linear or cyclic alkano- or alkenophenones

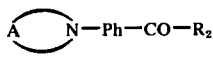

may be reduced either with lithium aluminum hydride or with $R_1$-magnesium halides, or

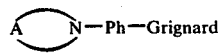

compounds reacted with $R_1$—CO—$R_2$, to yield the corresponding benzyl alcohols, whose hydroxy group may be reactively esterified or salified according to well-known methods, e.g. by reaction with phosphorus, thionyl or sulfonyl halides, alkali or alkaline earth metals respectively and the resulting esters or salts may be converted into ethers either by reaction with alcoholates or reactive esters respectively. The compounds in which $Y_2$ is an ammonium group, can be obtained from the former reactive esters and secondary amines and the resulting tertiary amines are quaternized in the usual manner, e.g. by reaction with lower alkyl or aralkyl halides.

The starting material containing $Y_3$ can be obtained from the former compounds in which $Y_2$ is a metallic group, by reacting them with a methyl halide, formaldehyde, a formyl halide, lower alkanal, alkenyl or hydroxyalkanal or a lower alkanoyl, alkenoyl or oxalyl halide respectively and, if desired, dehydrating resulting alcohols by the action of acidic agents, e.g. sulfuric acid or phosphorus pentoxide, to yield unsaturated derivatives thereof. The latter, e.g. methylidene compounds, may be reacted with boranes in order to obtain borylmethyl compounds and aldehydes with hydroxylamine, to yield the hydroxyiminomethyl compounds (oximes). The aldehydes, i.e. compounds in which $Y_3$ is formyl, can also be obtained from said ketones

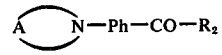

by reaction with dimethylsulfoniummethylide or dimethyloxysulfoniummethylide (generated from the corresponding trimethylsulfonium salts) and rearranging the resulting ethyleneoxides to the corresponding aldehydes by the action of Lewis acids, e.g. p-toluene sulfonic acid or boron trifluoride, or according to the Darzens condensation by reacting the above ketones with α-halo-alkanoic or alkenoic acid esters in the presence of alcoholates, e.g. potassium tert. butoxide, saponifying the glycidic esters formed and rearranging and decarboxylating them, advantageously in acidic media, e.g. sulfuric acid.

The starting material containing $Y_4$, which represents free, esterified or etherified hydroxy or mercapto, can be prepared according to the cyanohydrin or analog syntheses, e.g. by reaction of compounds

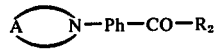

or their thiono analogs, with aqueous potassium cyanide under acidic conditions and, if desired, converting resulting nitriles into other acid derivatives and/or alcohols into corresponding mercapto compounds or reactive esters or ethers thereof, or dehydrating them to unsaturated derivatives. The compounds in which $Y_5$ is oxo or thiono an be obtained according to Friedel-Crafts with the use of suitable

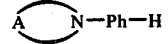

compounds and oxalyl halides. The resulting phenylglyoxylic acid esters may then be reduced with $R_2$—Grignard compounds, if desired, followed by dehydration. Said compounds may also be prepared according to the Ando synthesis by reaction with mesoxalates in the presence of stannic chloride. The resulting adduct can either be hydrogenated, the malonate formed metallized and reacted with a reactive ester of $R_2$—OH or saponified and decarboxylated.

Finally the α-diazoketones are obtained from corresponding benzoic acid halides and $R_2$-diazo compounds and the α-haloketones by halogenating of the corresponding alkanophenones or reacting the former α-diazoketones with hydrohalic acids. The starting material of Formula IV is prepared analogous to the process mentioned under item a), by selecting starting materials containing $X_2$ or a group capable of being converted into $X_2$, advantageously nitro, instead

The pharmacologically active compounds of the invention are useful in the manufacture of pharmaceutical compositions containing an effective amount thereof in conjunction or admixture with excipients suitable for either enteral, parenteral or topical application. Preferred are tablets and gelatin capsules comprising the active ingredient together with a) diluents, e.g. lactose, dextrose, sucrose, mannitol, sorbitol, cellulose and/or glycine, b) lubricants, e.g. silica, talcum, stearic acid, its magnesium or calcium salt and/or polyethyleneglycol, for tablets also c) binders, e.g. magnesium aluminum silicate, starch paste, gelatin, tragacanth, methylcellulose, sodium carboxymethylcellulose and/or polyvinylpyrrolidone, if desired, d) disintegrants, e.g. starches, agar, alginic acid or its sodium salt, enzymes of the binders or effervescent mixtures and/or e) adsorbents, colorants, flavors and sweeteners. Injectable compositions are preferably aqueous isotonic solutions or suspensions, and suppositories or ointments are advantageously fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75 percent, preferably about 1 to 50 percent of the active ingredient.

The following examples are intended to illustrate the invention and are not to be construed as being limitations thereon. Temperatures are given in degrees Centigrade, and all parts wherever given are parts by weight.

EXAMPLE 1

The mixture of 10.8 g ethyl 4-amino-phenylacetate hydrochloride, 32.4 g 1,4-dibromo-2-butene, 84 g sodium bicarbonate and 500 ml dimethylformamide is refluxed for 6 hours while stirring, filtered hot and the filtrate evaporated in vacuo. The residue is taken up in 150 ml 25 percent aqueous sodium hydroxide, the mixture refluxed for 1 hour, cooled and washed with diethyl ether. It is adjusted to pH 5 with hydrochloric acid, extracted with diethyl ether, the extract dried, filtered and evaporated, to yield the 4-pyrrolinophenylacetic acid of the formula

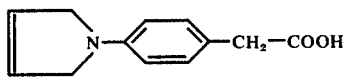

melting at 162°–165°.

EXAMPLE 2

To the stirred mixture of 5.5 g ethyl 4-pyrrolinophenylacetate, 100 ml dimethylformamide and 100 ml toluene, 1.25 g 54 percent sodium hydride in mineral oil are added portionwise and stirring is continued for 1½ hour at room temperature. Hereupon the solution of 6.8 g methyl iodide in 25 ml toluene is added dropwise during 20 minutes and the mixture is stirred overnight at room temperature. It is evaporated in vacuo, the residue taken up in 75 ml 10 percent aqueous potassium hydroxide and the mixture heated at the steam cone for 2 hours. It is cooled, adjusted to pH 5 with hydrochloric acid, extracted with diethyl ether; the extract is dried, concentrated, the concentrate diluted with petroleum ether, and the precipitate formed filtered off, to yield the α-(4-pyrrolinophenyl)-propionic acid of the formula

melting at 197°–199° after recrystallization from ethanol.

By replacing in this example the methyl iodide by an equivalent amount of ethyl iodide, allyl bromide, 3-cyclopentenyl bromide or cyclopropylmethyl bromide, the ethyl α-(4-pyrrolinophenyl)-(butyrate, 4-pentenoate, α-3-cyclopentenylacetate or α-cyclopropylmethylacetate) are obtained.

The 3- or 4-amino-phenylacetic or -α-phenylpropionic acid ethyl esters, sodium salts or the 2-, 3- or 4-chlorinated derivatives thereof, can also be reacted with 1,4-dibromo-2-butene, 1,5-dibromo-2-pentene or 1,6-dibromo-3-hexene in the presence of sodium bicarbonate, as shown in Example 1, to yield inter alia the ethyl 3- or 4-(pyrrolino, 2-pentenyleneimino or 3-hexenyleneimino)-phenylacetate or -α-phenylpropionate or the corresponding 4- or 3-chloro derivatives thereof.

The 3- or 4-amino-phenylacetic or -α-phenyl-propionic acid or the 2-, 3- or 4-chlorinated derivatives thereof, can also be reacted with aliphatic dicarboxylic acid dichlorides or anhydrides, e.g. maleic or glutaconic acid anhydride, to yield inter alia the α-[4-(2,5-dioxo-pyrrolino)-phenyl]-propionic acid, 4-(2,6-dioxo-hex-3-enyleneimino)-phenylacetic acid or α-[3-chloro(2,6-dioxo-hex-3-enyleneimino)-phenyl]-propionic acid.

Moreover, the 4-fluoro-phenyl-acetonitrile can be reacted with 4-oxo-piperidine, to yield the 4-(4-oxo-piperidino)-phenyl-acetonitrile, which can be hydrolyzed to the free acid and the acid esterified, or the ethyl α-(3-chloro-4-aminophenyl)-propionate reacted with 4-oxo-2,5-heptadienedioic acid diethyl ester, saponifying and decarboxylating the reaction product, to yield the α-[3-chloro-4-(4-oxo-piperidino)-phenyl]-propionic acid. In corresponding esters, the carbonyl group can be reduced with one equivalent of Grignard compounds, e.g. methyl-, ethyl-, n-propyl-, phenyl- or 4-chlorophenyl-magnesium bromide, to yield, inter alia, the ethyl 4-[4-hydroxy-4-(methyl, ethyl, n-propyl, phenyl or 4-chlorophenyl)-piperidino]-phenyl acetate or α-[3-chloro-4-(4-hydroxy-4-methylpiperidino)-phenyl]-propionate. Said esters or the corresponding acids can be dehydrated wtih sulfuric or phosphoric acid, to yield, for example, the 4-(3-n-propyl-pent-2-enyleneimino)-phenylacetic acid or the α-[3-chloro-4-(3-methylpent-2-enyleneimino)-phenyl]-phenyl]-propionic acid.

EXAMPLE 3

To the mixture of 85.5g ethyl α-(3-chloro-4-aminophenyl)-propionate hydrochloride, 142 g sodium carbonate and 600 ml dimethyl formamide, 107 g 1,4-dibromo-2-butene are added dropwise while stirring and the whole is refluxed for 5 hours and allowed to stand overnight at room temperature. The mixture is filtered, the filtrate evaporated in vacuo, the residue is triturated with hexane, the mixture filtered, the residue washed with petroleum ether and the filtrate evaporated. The residue is combined with 280 ml 25 percent aqueous sodium hydroxide and the mixture refluxed for 8 hours. After cooling, it is diluted with water, washed with diethyl ether, the pH adjusted to 5–5.2 with hydrochloric acid and extracted with diethyl ether. The extract is dried, filtered, evaporated and the residue recrystallized from benzene-hexane, to yield the α-(3-chloro-4-pyrrolinophenyl)-propionic acid of the formula

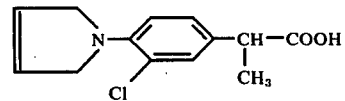

melting at 94°–96°. The starting material is prepared as follows:

To the solution of 52 g ethyl 4-nitrophenylacetate in 350 ml dimethylformamide-toluene (1:1), 9.5 g of 50 percent sodium hydride in mineral oil are added portionwise while stirring and cooling. After 1½ hours stirring at room temperature, 26 g methyl iodide are added dropwise and the mixture is stirred overnight at room temperature. The mixture is carefully combined with water, extracted with diethyl ether, the extract dried, filtered and evaporated. The residue is taken up in 100 ml ethanol, the solution seeded with a few crystals starting material and allowed to stand in the cold. The precipitate formed is filtered off and the filtrate evaporated, to yield the ethyl α-(4-nitrophenyl)-propionate.

50 g thereof are hydrogenated in 200 ml 95 percent aqueous ethanol over 0.4 g palladium on charcoal until the hydrogen uptake ceases. The mixture is filtered and the filtrate evaporated, to yield the ethyl α-(4-aminophenyl)-propionate; (its hydrochloride melts at 137°–140°). 25 g thereof are combined with 100 ml acetic acid anhydride while stirring and cooling and the mixture is allowed to stand for one hour at room temperature. It is evaporated in vacuo and the residue recrystallized from diethyl ether, to yield the ethyl α-(4-acetylaminophenyl)-propionate melting at 88°–90°.

Through the solution of 25 g thereof in 100 ml acetic acid, chlorine is bubbled while stirring and cooling and the course of chlorination is followed by a thin layer chromotography on silica gel in hexane-diethyl ether (1:4). After the consumption of starting material, the mixture is evaporated in vacuo, the residue taken up in 150 ml ethanol and hydrogen chloride is bubbled through the solution for 45 minutes. After refluxing for 15 hours, it is evaporated and the residue recrystallized from ethanoldiethyl ether, to yield the ethyl α-(3-chloro-4-aminophenyl)-propionate hydrochloride, melting at 164°–168°.

EXAMPLE 4

To the solution of 25.1 g d,l-α-(3-chloro-4-pyrrolinophenyl)-propionic acid (Example 3) in 450 diethyl ether, 17.1 g d-α-(1-naphthyl)-ethylamine are added while stirring and the mixture is evaporated in vacuo. The residue is recrystallized 7 times from ethanol-diethyl ether, to yield the corresponding salt melting at 133°–135°. 5 g thereof are dissolved in the minimum amount of 5 percent sodium hydroxide, the solution washed with diethyl ether, its pH adjusted to 5.5 with hydrochloric acid and extracted with diethyl ether. The extract is dried, filtered and evaporated, to yield the d-α-(3-chloro-4-pyrrolinophenyl)-propionic acid having $[\alpha]_D^{25} = + 34.8°$ (ethanol).

EXAMPLE 5

The mixture of 10 g ethyl 4-aminophenylacetate, 16.4 g α,α'-dibromo-o-xylene, 17.8 g sodium carbonate and 250 ml dimethylformamide is refluxed for 6 hours while stirring. After cooling, it is diluted with water, extracted with diethyl ether, the extract washed with water, dried, filtered, evaporated and the residue recrystallized from diethyl ether, to yield the ethyl 4-isoindolinophenylacetate of the formula

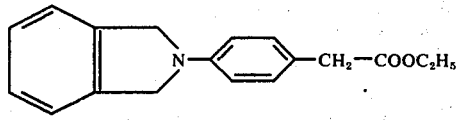

melting at 118°–120°.

EXAMPLE 6

The commercial 1,4-dibromo-2-butene, containing mainly the trans epimer and being used in Examples 1 and 3, may be replaced by pure cis-1,4-dichloro-2-butene. The mixture of 11.3 g thereof, 15.7 g ethyl α-(4-aminophenyl)-propionate, 100 ml dimethylformamide and 10.6 g sodium carbonate is refluxed for 5 hours while stirring and allowed to stand overnight at room temperature. It is filtered, the filtrate evaporated in vacuo, the residue taken up in 260 ml 25 percent aqueous sodium hydroxide and the mixture refluxed for 8 hours. It is cooled, diluted with water, washed with diethyl ether and the pH adjusted to about 5 with hydrochloric acid. The mixture is extracted with diethyl ether, the extract dried, evaporated and the residue recrystallized from ethanol, to yield the α-(4-pyrrolinophenyl)-propionic acid melting at 197°–199°; it is identical with that obtained according to Example 2.

EXAMPLE 7

The mixture of 13.2 g ethyl α-(3-chloro-4-aminophenyl)-propionate hydrochloride, 7.4 g phthalic anhydride, 10.1 g triethylamine and 200 ml toluene is refluxed for 6 hours and evaporated in vacuo. The residue is taken up in water, the mixture extracted with diethyl ether, the extract dried, filtered, evaporated and the residue recrystallized from diethyl ether, to yield the ethyl α-[3-chloro-4-(1,3-dioxo-isoindolino)-phenyl]-propionate of the formula

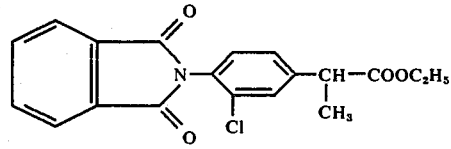

melting at 107°–110°.

EXAMPLE 8

The mixture of 11.9 g ethyl α-(4-aminophenyl)-β-cyclopropylpropionate, 14.2 g cis-1,4-dichloro-2-butene, 19 g sodium carbonate and 250 ml dimethylformamide is refluxed for 6 hours while stirring. After cooling, it is filtered, the filtrate evaporated in vacuo and the residue recrystallized from hexane, to yield the ethyl α-(4-pyrrolinophenyl)-β-cyclopropylpropionate of the formula

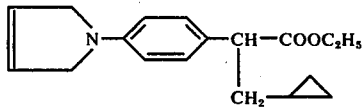

melting at 56°–58°.

The starting material is prepared as follows:

To the solution of 10 g ethyl 4-nitrophenylacetate in 400 ml dimethylformamide-toluene (1:1), 2.5 g 50 percent sodium hydride are added portionwise during 15 minutes while stirring and cooling with ice, after which the solution of 9.6 g cyclopropylmethyl bromide in 50 ml toluene is added dropwise and the mixture stirred overnight at room temperature. It is diluted with 200 ml water, extracted with diethyl ether, the extract dried, evaporated, the residue distilled and the fraction boiling at 132°–138°/0.25 mm Hg collected, to yield the ethyl α-(4-nitrophenyl)-β-cyclopropylpropionate.

The solution of 9 g thereof in 100 ml ethanol is hydrogenated over 0.5 g 10 percent palladium on charcoal until the theoretical amount of nitrogen has been absorbed. The mixture is filtered, the filtrate evaporated in vacuo, the residue taken up in diethyl ether, the solution gassed with hydrogen chloride, the precipitate formed filtered off and recrystallized from ethyl acetate, to yield the ethyl α-(4-aminophenyl)-β-cyclopropylpropionate hydrochloride melting at 160°–162°.

EXAMPLE 9

The mixture of 0.5 g ethyl α-(4-aminophenyl)-isobutyrate, 0.4 g cis-1,4-dichloro-2-butene, 0.4 g sodium carbonate and 20 ml dimethylformamide is refluxed for 10 hours, cooled and filtered. The filtrate is evaporated in vacuo, the residue distilled and the fraction boiling at 98°/0.22 mm Hg collected, to yield the ethyl α-(4-pyrrolinophenyl)-isobutyrate of the formula

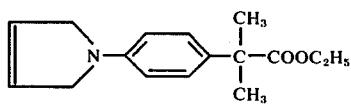

The starting material is prepared according to the method described in Example 3, but using 30.5 g methyl iodide instead of 26 g. By this variation, a mixture of ethyl α-(4-aminophenyl)-propionate and -isobutyrate is obtained. The mixture of 4 g thereof (containing about 20 percent of the latter), 1.1 g potassium hydroxide, 250 ml ethanol and 5 ml water is refluxed for 1½ hours, cooled, diluted with water and extracted with diethyl ether. The extract is dried, evaporated, the residue distilled and the fraction boiling at 308°–310°/760 mm Hg collected, to yield the ethyl-α-(4-aminophenyl)-isobutyrate.

EXAMPLE 10

The mixture of 4.6 g ethyl 4-isoindolinophenylacetate (Example 5) and 80 ml 25 percent aqueous sodium hydroxide is refluxed for 3 hours, cooled and diluted with water. The mixture is acidified with hydrochloric acid, the precipitate formed filtered off and recrystallized from ethyl acetate, to yield the 4-isoindolinophenylacetic acid melting at 237°–239°.

EXAMPLE 11

The mixture of 3 g ethyl α-(4-pyrrolinophenyl)-β-cyclopropylpropionate (Example 8) and 40 ml 25 percent aqueous sodium hydroxide is refluxed for 3 hours, cooled and diluted with water. It is acidified with hydrochloric acid, the precipitate formed filtered off and recrystallized from diethyl ether, to yield the α-(4-pyrrolinophenyl)-β-cyclopropylpropionic acid melting at 135°–137°.

EXAMPLE 12

The mixture of 10 g ethyl α-(4-aminophenyl)-propionate hydrochloride, 15 g α,α'-dibromo-o-xylene, 16.5 g sodium carbonate and 250 ml dimethylformamide is refluxed for 5 hours while stirring. After cooling, it is filtered, the filtrate concentrated in vacuo, the concentrate diluted with water, extracted with diethyl ether, the extract washed with water, dried, filtered and concentrated in vacuo. The precipitate formed is filtered off and recrystallized from ethanol. It is taken up in the minimum amount of benzene, the solution poured on a small column with silica gel and eluated with benzene. The first eluate is evaporated and the residue recrystallized from ethanol, to yield the ethyl α-(4-isoindolinophenyl)-propionate of the formula

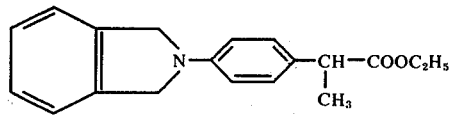

melting at 111°–113°.

The mixture of 1.8 g thereof, 5 ml 50 percent aqueous sodium hydroxide, 15 ml water and 100 ml ethanol is refluxed for 1½ hour and concentrated in vacuo. The concentrate is diluted with water, the suspension obtained acidified with 6N hydrochloric acid to pH3 and the mixture extracted with ethyl acetate. The extract is dried, filtered, evaporated in vacuo and the residue recrystallized from ethyl acetate, to yield the α-(4-isoindolinophenyl)-propionic acid melting at 247°–250°.

EXAMPLE 13

The mixture of 5 g ethyl 4-aminophenylacetate, 4.9 g homophthalic anhydride, 100 ml toluene and 0.5 ml triethylamine is refluxed overnight at the water trap and evaporated in vacuo. The residue is recrystallized from ethanol with the use of charcoal, to yield the ethyl 4-(1,3-dioxo-1,2,3,4-tetrahydroisoquinolino)phenyl acetate of the formula

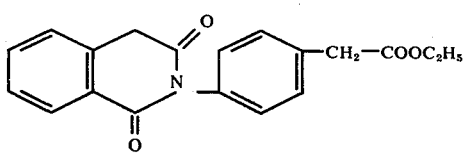

melting at 89°–91°.

EXAMPLE 14

To the solution of 0.5 g ethyl α-(4-isoindolinophenyl)-propionate in 50 ml glacial acetic acid, 6 ml of glacial acetic acid saturated with chlorine are added dropwise while stirring and the mixture is evaporated in vacuo. The residue is taken up in aqueous sodium bicarbonate, the mixture extracted with diethyl ether, the extract dried, filtered and evaporated. The residue is chromatographed on silica gel using benzene-hexane (1:1) as the mobile phase, to yield as the major product the ethyl α-(3-chloro-4-isoindolinophenyl)-propionate of the formula

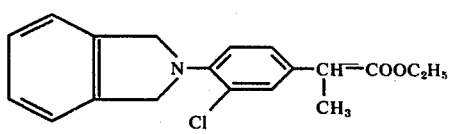

moving 30 mm (as compared to 26 mm for the starting material) and a minor portion of the ethyl α-(3,5-dichloro-4-isoindolinophenyl)-propionate of the formula

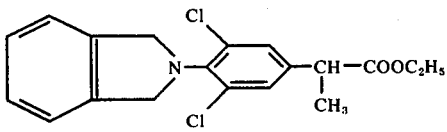

moving 39.5 mm in said system.

EXAMPLE 15

To the mixture of 5 g α-(3-chloro-4-pyrrolinophenyl)-propionic acid, 200 ml 1,2-dichloroethane and 42.6 g anhydrous disodium phosphate, the solution of trifluoroperacetic acid (prepared from 2.1 ml 90 percent aqueous hydrogen peroxide and 12.6 ml trifluoroacetic anhydride in 50 ml 1,2-dichloroethane) is added during 40 minutes while stirring at −5° to 0°. After 2 hours, 300 g ice are added, the organic phase separated and the aqueous layer extracted with methylene chloride. The combined organic solutions are dried, filtered and concentrated, to yield the α-(3-chloro-4-pyrrolinophenyl)-propionic acid N-oxide of the formula

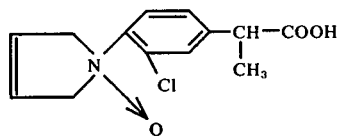

melting at 140°–142°.

EXAMPLE 16

To the mixture of 9.8 g maleic anhydride and 150 ml diethyl ether, the solution of 17.9 g ethyl 4-aminophenylacetate in 150 ml diethyl ether is added dropwise while stirring at room temperature. After 1½ hour, the mixture is cooled, filtered and the residue recrystallized from acetone, to yield the ethyl-4-(β-carboxyacryloxylamino)-phenyl-acetate melting at 152°–154°; (the analogously prepared α-[4-(β-carboxyacryloylamino)-phenyl]propionate melts at 128°–130° after recrystallization from diethyl ether, and its 3-chloro derivative melts at 86°–88° after recrystallization from hexane-diethyl ether).

The mixture of 14 g thereof, 50 ml acetic anhydride and 4 g sodium acetate is heated on a steam bath for 45 minutes and poured onto ice water. It is filtered and the residue recrystallized from cyclohexane, to yield the ethyl 4-(2,5-dioxopyrrolino)-phenylacetate of the formula

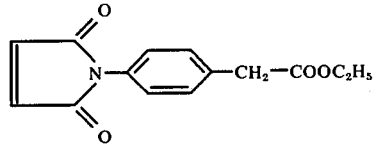

melting at 77°–79°.

The analogously prepared propionate melts at 87°–89° (hexane).

EXAMPLE 17

The mixture of 24 g ethyl α-(4-amino-3-chlorophenyl)-butyrate, 21 g sodium carbonate, 25 g cis-1,4-dichloro-2-butene and 250 ml dimethylformamide is refluxed for 12 hours. After cooling, it is diluted with diethyl ether, filtered and the filtrate evaporated. 11 g of the residue are taken up in 100 ml ethanol and 20 ml 25 percent aqueous sodium hydroxide, the mixture refluxed for 6 hours and evaporated in vacuo. The residue is taken up in water, the solution washed with diethyl ether, the pH adjusted to 5.5 with hydrochloric acid and extracted with diethyl ether. The extract is dried, evaporated and the residue recrystallized from hexane, to yield the α-(3-chloro-4-pyrrolinophenyl)-butyric acid of the formula

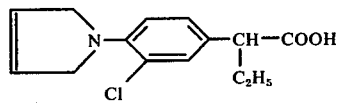

melting at 103°–105°.

The starting material is prepared as follows: To the mixture of 104 g ethyl 4-nitrophenyl-acetate, 350 ml dimethylformamide and 350 ml toluene, 19 g 50 percent sodium hydride in mineral oil are added during ¾ hour at 10° while stirring. After 1½ hours, 78 g ethyl iodide are added during 1 hour while stirring. After 1½ hours, some water is added dropwise and the mixture acidified with 10 percent hydrochloric acid. The mixture is extracted with diethyl ether, the extract dried and evaporated, to yield the ethyl α-(4-nitrophenyl)-butyrate.

The mixture of 115 g thereof, 400 ml 95 percent ethanol and 1.5 g palladium on charcoal is hydrogenated at 3 at. and room temperature. After the hydrogen uptake has ceased, the mixture is filtered, the filtrate evaporated, the residue taken up in 2N hydrochloric acid, the solution washed with diethyl ether, made basic with aqueous sodium hydroxide, extracted with diethyl ether and the extract evaporated, to yield the ethyl α-(4-aminophenyl)-butyrate.

The mixture of 35 g thereof and 100 ml acetic anhydride is stirred for 1 hour at the steam bath and evaporated, to yield the ethyl α-(4-acetylaminophenyl)-butyrate.

Through the solution of 35 g thereof in 200 ml acetic acid, chlorine is bubbled at 15°–20° while stirring and the course of the reaction followed by thin layer chromatography on silica gel in hexane-diethyl ether (1:4). After the consumption of starting material, the mixture is evaporated, to yield the ethyl α-(4-acetylamino-3-chlorophenyl)-butyrate hydrochloride.

Through the solution of 36 g thereof in 200 ml ethanol, hydrogen chloride is bubbled through while stirring for 45 minutes. The mixture is refluxed for 20 hours, allowed to stand for 24 hours at room temperature and evaporated. The residue is taken up in water, the solution made basic with aqueous sodium hydroxide, extracted with diethyl ether, the extract dried, evaporated, the residue distilled and the fraction boiling at 130°–132°/0.4 mm Hg collected, to yield the ethyl α-(4-amino-3-chlorophenyl)-butyrate.

EXAMPLE 18

The mixture of 0.63 g methyl α-cyclopropyl-(4-amino-3-chlorophenyl)-acetate hydrochloride, 0.55 g cis-1,4-dichloro-2-butene, 0.7 g sodium carbonate and 50 ml dimethylformamide is refluxed under nitrogen for 10 hours and stirred at room temperature for 2 days. It is filtered, the filtrate evaporated, the residue taken up in water, the mixture extracted with diethyl ether and the extract evaporated in vacuo. The residue is taken up in 35 ml ethanol, 0.5 ml water and 0.28 g potassium hydroxide are added, the mixture refluxed for 2 hours and evaporated in vacuo. The residue is taken up in water, the solution washed with diethyl ether, the pH adjusted to 4–4.5 with hydrochloric acid and the mixture extracted with ethyl acetate. The extract is dried, evaporated and the residue recrystallized from diethyl ether, to yield the α-cyclopropyl-(3-chloro-4-pyrrolinophenyl)-acetic acid of the formula

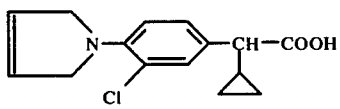

melting at 152°–156°.

The starting material is prepared as follows: To the solution of 200 g α-cyclopropyl-phenylacetic acid in 1.2 liters trifluoroacetic acid, the mixture of 73 ml 70 percent aqueous nitric acid and 9.1 ml 96 percent aqueous sulfuric acid is added dropwise while stirring and cooling to about 3°. After 1½ hours, the temperature is allowed to rise to room temperature and the mixture stirred for a total of 3 additional hours. It is dropped onto 3.2 kg ice and 300 ml water while stirring, filtered, the residue washed with 6 liters water and dried, to yield an about 2:1 mixture of α-cyclopropyl-(4- and 2-nitrophenyl)-acetic acid.

The mixture of 50 g thereof, 5 g 10 percent palladium on charcoal and 550 ml 95 percent aqueous ethanol is hydrogenated at atmospheric pressure until 15.9 liters hydrogen have been consumed. It is filtered, the filtrate concentrated, the precipitate formed in the cold separated and recrystallized once more from ethanol, to yield the pure α-cyclopropyl-(4-aminophenyl)-acetic acid.

To the mixture of 10 g thereof and 75 ml methanol, 75 ml saturated methanolic hydrogen chloride are added while stirring and cooling in an ice bath. After ½ hour, the mixture is heated to 38° for 1 hour and stirred at room temperature overnight. It is cooled, combined with 100 ml water and 105 ml 20 percent aqueous sodium hydroxide are added while cooling and stirring. The precipitate formed is filtered off, washed with water and dried, to yield the methyl α-cyclopropyl-(4-aminophenyl)-acetate, melting at 68°–69°.

The mixture of 12 g thereof and 100 ml acetic anhydride is stirred for 1 hour at the steam bath and evaporated. The residue is taken up in benzene and the mixture again evaporated, to yield the methyl α-cyclopropyl-(4-acetylaminophenyl)-acetate melting at 159°–162°.

To the solution of 1.6 g thereof in 50 ml acetic acid, 30 ml of a saturated solution of chlorine in acetic acid is added dropwise while stirring and the mixture evaporated in vacuo. The residue is taken up 2 times in benzene and the mixture evaporated, to yield the methyl α-cyclopropyl-(4-acetylamino-3-chlorophenyl)-acetate.

Through the solution of 1.6 g thereof in 200 ml methanol, hydrogen chloride is bubbled for 15 minutes and the mixture refluxed for 21 hours. It is evaporated in vacuo, the residue taken up in 6N hydrochloric acid, the mixture washed with diethyl ether, made basic with aqueous sodium hydroxide and extracted with diethyl ether. The extract is dried, evaporated, the residue taken up in diethyl ether, the solution acidified with ethereal hydrogen chloride and the precipitate formed filtered off, to yield the methyl α-cyclopropyl-(4-amino-3-chlorophenyl)-acetate hydrochloride melting at 164°–169°.

EXAMPLE 19

To the suspension of 4.37 g α-(3-chloro-4-pyrrolinophenyl)-propionic acid in 30 ml water, 50 percent aqueous sodium hydroxide is added dropwise until dissolution occurs and the pH is about 12.5. The solution is evaporated at 0.8 mm Hg, the residue taken up in isopropanol, the mixture filtered and the filtrate concentrated. The precipitate formed upon cooling and seeding is filtered off, dried overnight at 0.8 mm Hg at 90°, to yield the sodium α-(3-chloro-4-pyrrolinophenyl)-propionate of the formula

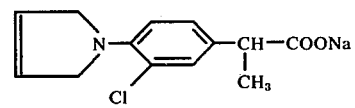

melting at 207°–209°.

EXAMPLE 20

3 g of the lithium salt of the ethyl 4-(4-oxopiperidino)-phenylacetate-N-p-toluenesulfonylhydrazone is slowly heated first to about 30°–40° and 0.3 mm Hg to effect final drying, and then to 80°–135° for 45 minutes. The residue is taken up in the minimum amount of ethanol, the solution poured on a small column with silica gel and eluted with benzene. The first eluate obtained is evaporated, to yield the ethyl 4-piperideino-phenylacetate of the formula

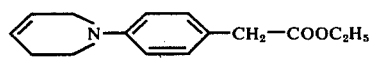

showing in the I.R. spectrum bands at 5.86 and 6.08 μ.

The starting material is prepared as follows: The mixture of 89.6 g ethyl 4-aminophenylacetate, 400 g ethyl acrylate and 100 ml acetic acid is refluxed for 19 hours and concentrated in vacuo. The concentrate is poured onto 500 ml ice water, the mixture made basic with aqueous sodium hydroxide and extracted with diethyl ether. The extract is dried, filtered, evaporated, the residue distilled and the fraction boiling at 211°–213°/0.6 mm Hg collected, to yield the ethyl 4-(bis-carbethoxyethylamino)-phenylacetate.

To the solution of 38 g thereof in 100 ml ethanol, that obtained from 3.4 g sodium and 100 ml ethanol is added dropwise and the mixture refluxed for 7 hours. It is evaporated in vacuo, the residue taken up in water, the mixture extracted with diethyl ether, the extract dried, filtered and evaporated, to yield the ethyl 4-(3-carbethoxy-4-oxopiperidino)-phenylacetate.

The mixture of 30.5 g thereof and 300 ml 50 percent sodium hydroxide is heated at the steam cone for 12 hours. It is cooled, acidified with concentrated hydrochloric acid and the mixture heated for 6 hours. It is evaporated in vacuo, the residue taken up in ethanolic hydrogen chloride, the mixture evaporated again, the residue taken up in the water, the mixture made basic with aqueous sodium hydroxide, extracted with diethyl ether, the extract dried and evaporated, to yield the ethyl 4-(4-oxopiperidino)-phenylacetate.

The mixture of 5.2 g thereof, 2.1 g 4-p-toluenesulfonylhydrazide, 3 ml glacial acetic acid and 50 ml ethanol is refluxed for 30 minutes. It is cooled, the precipitate formed filtered off and taken up in the minimum amount of tetrahydrofuran. To the solution, 13 ml 1.6N n-butyl lithium are added dropwise while still under nitrogen at 0°–5°. After 30 minutes, the mixture is evaporated at a temperature below 35°, to yield the lithium salt of the ethyl 4-(4-oxopiperidino)-phenylacetate-N-p-toluenesulfonylhydrazone.

EXAMPLE 21

Preparation of 10,000 tablets each containing 25.0 mg of the active ingredient:

| Formula: | |
| --- | --- |
| α-(3-chloro-4-pyrrolino-phenyl)-propionic acid | 250.00 g |
| Lactose | 1,956.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 45 ml water and the suspension added to the boiling solution of the polyethylene glycol in 180 ml water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

In the analogous manner, tablets can be prepared containing the same amount of another preferred drug substance of Formula II, e.g. the α-(4-pyrrolinophenyl)-propionic acid.

EXAMPLE 22

Preparation of 1,000 tablets, each containing 25 mg of the active ingredient:

| Formula | |
| --- | --- |
| α-(3-chloro-4-pyrrolino-phenyl)-propionic acid | 25.00 g |
| Lactose | 67.00 g |
| Corn Starch | 2.50 g |
| Polyethylene glycol 6,000 | 1.00 g |
| Talcum powder | 1.50 g |
| Magnesium stearate | 0.25 g |
| Stearic acid | 0.25 g |
| Cellulose powder | 2.50 g |

Procedure

All the powders are passed through a screen with openings of 0.6 mm. Then the carrier materials are blended and the drug substance is added gradually. After thorough mixing, the powder is compressed into tablets using concave punches with 4.8 mm diameter. Instead of the above drug substance, the corresponding sodium salt described in Example 19 can be used.

EXAMPLE 23

The starting material used in Example 3 can also be prepared as follows: 4.8 g 50 percent sodium hydride in mineral oil are added to 100 ml hexamethylphosphoramide while stirring under nitrogen. Hereupon 17.1 g diethyl α-methylmalonate are added and the mixture slowly heated to 100°. The solution of 19.2 g 2,4-dichloro-nitrobenzene in 20 ml hexamethylphosphoramide is added dropwise during ½ hour and the temperature kept at 100° for 7 hours. After cooling, the mixture is diluted with water, concentrated in vacuo, the residue taken up in water and extracted with benzene. The extract is washed with water, dried, filtered, evaporated, the residue distilled and the fraction boiling at 147°–148°/0.25 mm Hg collected, to yield the diethyl α-methyl-α-(3-chloro-4-nitrophenyl)-malonate. (The analogously prepared diethyl α-ethyl-α-(3-chloro-4-nitrophenyl)-malonate boils at 170°–174°/1 mm Hg.)

Through the solution of 4 g thereof in 50 ml anhydrous ethanol, hydrogen chloride is bubbled for 5 minutes. Hereupon 0.5 g 10 percent palladium on charcoal are added and the mixture hydrogenated for 10 minutes at an initial pressure of 3 at. It is filtered and the filtrate evaporated in vacuo. The residue is taken up in 5 percent aqueous sodium hydroxide, the mixture extracted with diethyl ether, the extract dried, filtered and evaporated, to yield the diethyl α-methyl-α-(3-chloro-4-aminophenyl)-malonate, showing in the I.R. spectrum bands at 1720, 3370 and 3460 cm$^{-1}$.

The mixture of 75 g thereof and 150 ml 50 percent aqueous sodium hydroxide is refluxed overnight, cooled, diluted with water and washed with diethyl ether. It is acidified with concentrated hydrochloric acid, the mixture again refluxed overnight and evaporated in vacuo. The residue is taken up in anhydrous ethanolic hydrogen chloride, the mixture refluxed for 6 hours, evaporated and the residue recrystallized from ethanol-diethyl ether, to yield the ethyl α-(3-chloro-4-aminophenyl)-propionate hydrochloride melting at 164°–168°.

EXAMPLE 24

The combined mother liquors obtained in the preparation of the d-α-(1-naphthyl)-ethylammonium d-α-(3-chloro-4-pyrrolinophenyl)-propionate, melting at 133°–135° and having $[\alpha]_D^{25} = +9.6°$ according to Example 4, are evaporated in vacuo and the residue taken up in water. The pH of the solution is adjusted to 5.5 with hydrochloric acid and extracted with diethyl ether. The extract is dried, filtered and evaporated. 8.4 g thereof are taken up in 20 ml diethyl ether and 5.7 g l-α-(1-naphthyl)-ethylamine in 35 ml diethyl ether are added. The precipitate formed is recrystallized 5 times from ethanol-diethyl ether, to yield the corresponding salt melting at 132°–133°, $[\alpha]_D^{25} = -9.1°$. 10 g thereof are dissolved in the minimum amount of 5 percent aqueous sodium hydroxide, the solution washed with diethyl ether, its pH adjusted to 5.5 with hydrochloric acid and extracted with diethyl ether. The extract is dried, filtered and evaporated, to yield the l-α-(3-chloro-4-pyrrolinophenyl)-propionic acid having $[\alpha]_D^{25} = -38.4°$ (ethanol, a more purified sample of its antipode has $[\alpha]_D^{25} = +39.6°$).

1 g. thereof is taken up in the minimum amount of water and the solution adjusted to pH = 8 with aqueous sodium hydroxide. The solution is evaporated in vacuo, the residue taken up in ethanol, filtered, the filtrate concentrated and the concentrate diluted with diethyl ether, to yield the sodium 1- α(3-chloro-4-pyrrolinophenyl)-propionate, melting at 205°–208°, $[\alpha]_D^{25} = +17.4°$. The analogously prepared sodium salt of the dextrorotatory acid of Example 4 melts at 212°–214°, $[\alpha]_D^{25} = -17.4°$.

EXAMPLE 25

The mixture of 7.6 g ethyl α-[3-chloro-4-(β-cis-carboxyacryloylamino)-phenyl]-propionate, 100 ml acetic anhydride and 3 g sodium acetate is heated at the steam cone for 1 hour, cooled and poured onto 300 g ice. The mixture is extracted with diethyl ether, the extract washed with water, dried, filtered and evaporated, to yield the ethyl α-[3-chloro-4-(2,5-dioxopyrrolino)-phenyl]-propionate of the formula

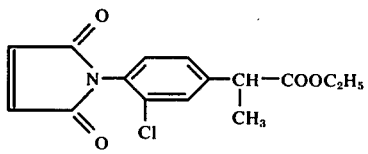

showing in the N.M.R. spectrum peaks at 1.2 (triplet), 1.5 (doublet), 3.7 (quartet) and 6.9 ppm (singlet).

The starting material is prepared as follows: To the solution of 7.4 g ethyl α-(4-amino-3-chlorophenyl)-propionate in 50 ml diethyl ether, 5 g maleic anhydride in 25 ml diethyl ether are added, the mixture slowly concentrated to 30 ml and diluted with hexane. After standing overnight at room temperature, the precipitate formed is filtered off, to yield the ethyl α- [3-chloro-4-(β-ciscarboxy-acryloylamino)-phenyl]-propionate, melting at 86-88°.

EXAMPLE 26

Preparation of 10,000 capsules each containing 25 mg of the active ingredient:

| Formula: | |
|---|---|
| α-(3-chloro-4-pyrrolinophenyl)-propionic acid | 250 g |
| Microcrystalline cellulose | 1,080 g |
| Hardened vegetable oil fraction melting at 65–80° | 20 g |

PROCEDURE:

All the powders are passed through a screen with openings of 0.6 mm. Then the drug substance is placed in a suitable mixer and mixed first with the oil fraction and then with the cellulose until homogeneous. 135 mg of the mixture are filled into 0.3 ml hard gelatine capsules, using a capsule filling machine.

EXAMPLE 27

The mixture of 12 g ethyl α-(4-amino-3-chlorophenyl)-propionate, 11.6 g α,α'-dibromo-o-xylene, 17 g sodium carbonate and 250 ml dimethylformamide is refluxed for 6 hours under nitrogen. After cooling it is filtered, the filtrate diluted with water, extracted with diethyl ether, the extract washed with water, dried, filtered and evaporated. The residue is distilled and the fraction boiling at 190°–200°/0.4 mmHg collected, to yield the ethyl α-(3-chloro-4-isoindolinophenyl)-propionate, which is identical with that obtained according to Example 14.

EXAMPLE 28

The mixture of 22.8 g ethyl α-(4-amino-3-chlorophenyl)-propionate, 19.8 g ethyl 2-chloromethylbenzoate, 15 ml triethylamine and 300 ml ethanol is allowed to stand overnight and slowly evaporated. The residue is taken up in water, the mixture extracted with diethyl ether, the extract washed with 5 percent hydrochloric acid and water, dried, filtered and evaporated. The residue is taken up in 250 ml ethanol, 100 ml 10 percent aqueous potassium carbonate are added and the mixture slowly evaporated in vacuo. The residue is taken up in water, the solution filtered, the pH of the filtrate adjusted to 4 with hydrochloric acid and extracted with ethyl acetate. The extract is washed with water, dried and concentrated, to yield the α-[3-chloro-4-(1-oxoisoindolino)-phenyl]-propionic acid of the formula

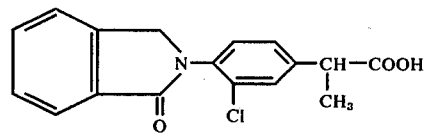

melting at 161°–163°.

The ethyl ester thereof can also be prepared by bubbling air through a concentrated solution of the compounds of Examples 14 or 27 in dimethylformamide for 2 hours at 60° while stirring. The mixture is evaporated in vacuo, the residue distilled and the fraction boiling at 200°–210°/0.4 mm Hg collected.

EXAMPLE 29

According to the methods described in the previous examples, the following compounds are prepared from equivalent amounts of the corresponding starting materials:

a. α-[3-chloro-4-(2-oxopyrrolino)-phenyl]-propionic acid;
b. α-[3-chloro-4-( 2-methyl-5-oxopyrrolino)-phenyl]-propionic acid;
c. α-[4-(3,4-dichloro-2,5-dioxopyrrolino)-phenyl]-propionic acid;
d. α-[3-chloro-4-(5-chloro-1-oxoisoindolino)-phenyl]-propionic acid;
e. α-[3-chloro-4-(6-pyrrolo[3,4-b]pyridyl)-phenyl]-propionic acid;
f. α-[3-chloro-4-(5- or 7-oxo-6-pyrrolo[3,4-b]pyridyl)-phenyl]-propionic acid;
g. α-[3-chloro-4-(5,7-dioxo-6-pyrrolo[3,4-b]pyridyl)-phenyl]-propionic acid, the methyl or ethyl esters thereof, or the sodium or potassium salts thereof.

EXAMPLE 30

Preparation of a cream containing 2% of the active ingredient.

| Formula: | |
|---|---|
| ethyl α-[3-chloro-4-(2,5-dioxo-pyrrolino)-phenyl]-propionate | 20 g |
| White Petrolatum | 50 g |
| Spermaceti | 40 g |
| Stearyl Alcohol | 50 g |
| Cetyl Alcohol | 50 g |
| Stearic Acid | 20 g |
| Glycerine | 120 g |
| Sodium Lauryl Sulfate | 10 g |
| Purified Water | 610 g |

PROCEDURE:

The mixture of the petrolatum, spermacetl, stearyl and cetyl alcohols and stearic acid is molten and the liquid strained into a mixing kettle heated to about 70°. The drug substance, admixed with the sodium lauryl sulfate, is suspended in the glycerine-water solution, which is heated to 72° and slowly added to the fats while mixing vigorously until a homogeneous cream has formed.

EXAMPLE 31

The mixture of 10 g ethyl [4-(α,β-dichloro-β-cis-carboxyacryloylamino)-phenyl]-acetate and 50 ml acetic anhydride is heated at the steam cone for 1 hour, cooled and poured onto 500 g ice. The mixture is extracted with diethyl ether, the extract dried, evaporated and the residue recrystallized from ethyl acetate. The crystals obtained are redissolved in diethyl etherethyl acetate (4:1) and the solution chromatographed on silica gel. The column is eluted with toluene-ethyl acetate (5:1), the solution evaporated and the residue recrystallized from toluene, to yield the ethyl [4-(3,4-dichloro-2,5-dioxopyrrolino)-phenyl]-acetate of the formula

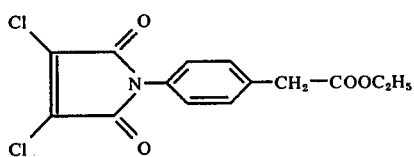

melting at 175°–177°.

The starting material is prepared as follows: To the solution of 8.95 g ethyl 4-aminophenylacetate in 50 ml diethyl ether, 8.42 g dichloromaleic anhydride in 50 ml methylene chloride are added and the mixture allowed to stand for 3 days at room temperature. The precipitate formed is filtered off and washed with diethyl ether, to yield the ethyl [4-(α,β-dichloro-β-ciscarboxyacryloylamino)-phenyl]-acetate melting at 123°–125°.

EXAMPLE 32

The mixture of 1 g ethyl α-(3-chloro-4-isoindolinophenyl)propionate, 50 ml ethanol and 15 ml 20 percent aqueous potassium carbonate is refluxed for 1 hour and evaporated in vacuo. The residue is taken up in water, the mixture acidified with 6N hydrochloric acid to pH = 3 and the mixture extracted with ethyl acetate. The extract is dried, filtered, evaporated and the residue recrystallized from ethyl acetate, to yield the α-(3-chloro-4-isoindolinophenyl)-propionic acid melting at 148°–150°.

EXAMPLE 33

Replacing the ethyl 2-chloromethylbenzoate in Example 28 by the equivalent amount of 2-chloromethylbenzoyl chloride and following the procedure given in said example, one obtains a more pure α-[3-chloro-4-(1-oxoisoindolino)-phenyl]-propionic acid melting at 178°–180°; its ethyl ester melts at 111°–113°.

EXAMPLE 34

According to the methods described in the previous examples, more particularly Examples 2,3,8,14,17,18 or 28, the following compounds of Formula II are prepared from equivalent amounts of the corresponding starting materials:

| No. | Am | $R_3$ | $R_4$ | m.p. acid | | m.p. ester |
|---|---|---|---|---|---|---|
| 1 | 3-methylpyrrolino | H | H | — | $C_2H_5$, | 45–48° |
| 2 | 3,4-dimethyl-2,5-dioxo-pyrrolino | H | H | — | " | 85–87° |
| 3 | 3,4-dichloro-2,5-dioxo-pyrrolino | $CH_3$ | H | — | " | 90° |
| 4 | " | " | Cl | — | " | 94–96° |
| 5 | pyrrolino | △ | H | 133–136° | $CH_3$, | 82–84° |
| 6 | 1-oxoisoindolino | H | H | 206–208° | $C_2H_5$, | 111–114° |
| 7 | " | $CH_3$ | H | 208–210° | " | 104–106° |
| 8 | isoindolino | " | Cl | 148–150° | " | 67–70° |
| 9 | 1-oxoisoindolino | $C_2H_5$ | Cl | 191–193° | " | b.p. 230–240°/0.35 mm |
| 10 | " | △ | Cl | 242–245° | " | b.p. 225–235°/0.33 mm |
| 11 | 4,5,6,7-tetrachloro-phthalimino | H | H | — | " | 197–199° |

EXAMPLE 35

The mixture of 18.4 g of 1,2,3,6-tetrahydro-phthalic acid anhydride, 17.9 g of ethyl 4-aminophenylacetate and 200 ml of methylene chloride is refluxed for 1 day and evaporated. The residual ethyl 4-(2-carboxy-4-cyclohexenylcarbamoyl)-phenylacetate is taken up in 100 ml of acetic acid anhydride, the mixture refluxed for 2 hours and evaporated. The residue is taken up in water, the mixture extracted with diethyl ether, the extract washed with water, dried, evaporated and the residue recrystallized from diethyl ether, to yield the ethyl 4-(1,3-dioxo-3a,4,7,7a-tetrahydroisoindolino)-phenylacetate of the formula

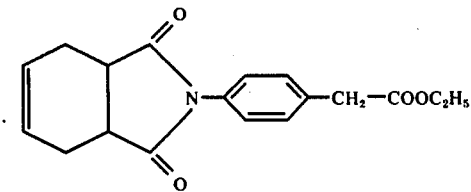

melting at 82°–83°.

EXAMPLE 36

The mixture of 7.9 g of ethyl α-(4-aminophenyl)-propionate and 8.3 g of ethyl 2-chloromethylbenzoate is refluxed under nitrogen for one hour. The residue is recrystallized from hexane, to yield the ethyl α-[4-(1-oxoisoindolino)-phenyl]-propionate of the formula

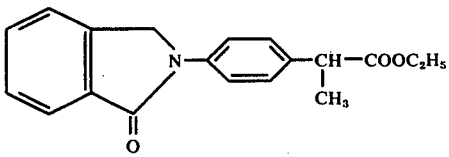

melting at 104°–106°.

The mixture of 4.5 g thereof, 1.6 g of potassium hydroxide, 2 ml of water and 250 ml of ethanol is refluxed under nitrogen for two hours and evaporated under reduced pressure. The residue is taken up in water, the solution washed with chloroform, acidified with hydrochloric acid and extracted with ethyl acetate. The extract is dried, evaporated and the residue recrystallized from ethyl acetate, to yield the corresponding free acid melting at 208°–210°.

In the analogous manner, the ethyl 4-(1-oxoisoindolino)phenylacetate, m.p. 111°–114° and the corresponding free acid, m.p. 206°–208°, are prepared.

EXAMPLE 37

The mixture of 24 g of ethyl α-[4-(3-oxo-isobenzofuran-1-ylamino)-phenyl]-propionate, 5.3 g sodium borohydride and 4 ml of ethanol is refluxed for one hour while stirring and allowed to stand overnight at room temperature. It is diluted with water, the pH thereof adjusted to 5.6 with hydrochloric acid and the solution extracted with ethyl acetate. The extract is dried, filtered and evaporated, to yield the ethyl α-[4-(1-oxisoindolino)phenyl]propionate, melting at 106°–109°. It is identical with that obtained according to Example 36. The starting material is prepared as follows:

The mixture of 17.7 g of ethyl α-(4-aminophenyl)-propionate, 15 g of 2-carboxy-benzaldehyde, 50 mg of p-toluenesulfonic acid and 400 ml of toluene is refluxed for two days on a water trap. After collection of the theoretical amount of water (1.9 ml), it is concentrated and the precipitate formed recrystallized from ethanol, to yield the ethyl α-[4-(3-oxo-isobenzofuran-1-ylamino)-phenyl]-propionate, melting at 136°–139°.

EXAMPLE 38

The mixture of α-[4-(1-oxoisoindolino)-phenyl]-propionyl chloride, 0.9 g of 4-chloro-aniline, 1.5 g of triethylamine and 100 ml of benzene is refluxed for one hour, filtered and the filtrate washed with water. It is dried, evaporated and the residue recrystallized from acetonitrile, to yield the N-(4-chlorophenyl)α-[4-(1-oxoisoindolino)-phenyl]-propionamide of the formula

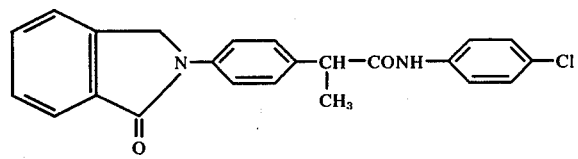

melting at 240°–242°.

The starting material is prepared as follows: The mixture of 2.0 g of α-[4-(1-oxoisoindolino)-phenyl]-propionic acid and 25 ml of thionyl chloride is refluxed for a half hour under nitrogen and evaporated under reduced pressure. The residue is taken up two times in benzene and the mixture again evaporated, to yield the corresponding acid chloride, melting at 129°–132°.

EXAMPLE 39

Analogous to the method described in the previous examples, advantageously according to Examples 18, 36 or 37 respectively, the following compounds of Formula II are obtained: Am = 1-oxoisoindolino, $R_4$ = H

| $R_3$ | m.p. acid | | m.p. ester |
|---|---|---|---|
| △ | 186–188° | $CH_3$, | 98–101° |
| '' | — | $C_2H_5$, | 111–113° |
| $CH_3$ | — | $CH_3$, | 129–132° |
| '' | — | $n-C_3H_7$, | 87–89° |
| '' | — | $i-C_3H_7$, | 118–121° |
| '' | — | $i-C_4H_9$, | 110–113° |

EXAMPLE 40

The mixture of 5 g of 2-(3-chloro-4-pyrrolinophenyl)-propanol, 4 g of sodium hydroxide and 50 ml of water is added to the stirred suspension prepared from 6.5 g of silver nitrate, 1.8 g of sodium hydroxide and 60 ml of water. After 3 hours, the mixture is filtered, the pH of the filtrate adjusted to 5.5 with hydrochloric acid and extracted with diethyl ether. The extract is washed with water, dried, filtered, evaporated and the residue recrystallized from toluene, to yield the α-(3-chloro-4-pyrrolinophenyl)-propionic acid, melting at 96°–98°.

The starting material is prepared as follows: The mixture of 68 g 4-aminoacetophenone and 100 ml acetic anhydride is refluxed for 2 hours. The excess acetic anhydride is removed by distillation and the residue is dissolved in acetic acid. Chlorine is passed into the above solution until one equivalent is taken up and the reaction mixture is evaporated, to yield the 4-acetylamino-3-chloro-acetophenone.

The solution of 106 g thereof in 200 ml tetrahydrofuran is added dropwise in a nitrogen atmosphere to methyl magnesium iodide (prepared from 13.4 g of magnesium turnings and 78.1 g methyl iodide in 300 ml tetrahydrofuran). The resulting mixture is refluxed for 18 hours, and on cooling 200 ml 10 percent aqueous hydrochloric acid is added and the mixture heated for an additional 2 hours. The tetrahydrofuran is distilled off and water is added to the residue. The aqueous mixture is extracted with diethyl ether and the ether extract is dried and evaporated. The residue is combined with 100 ml acetic anhydride and warmed on the steam bath for 1 hour. The solvent is distilled off azeotropically with toluene, to give the 2-(3-chloro-4-acetylaminophenyl)-propene.

To the solution of 80 g thereof in 100 ml of diethyleneglycol dimethyl ether, the mixture of 15 g sodium borohydride, 61 g borontrifluoride etherate and 100 ml diethyleneglycol dimethyl ether is added while stirring under nitrogen at 0°. The reaction mixture is warmed up to 25° and stirred for 2 hours. Ice chips are added to hydrolyze the excess diborane. On cooling, 100 ml 3N aqueous sodium hydroxide are added, followed by 50 ml 30 percent hydrogen peroxide over a period of 1 hour to the above mixture. After stirring for 2 hours at room temperature, the layers are separated and the aqueous layer extracted with diethyl ether. The combined ether extracts are evaporated and the residue dissolved in 100 ml ethanol and 100 ml 3N aqueous sodium hydroxide. The resulting mixture is refluxed for 2 hours, cooled, extracted with diethyl ether, the extract dried and evaporated, to give the 2-(3-chloro-4-aminophenyl)-propanol.

70 g thereof is heated at 100° for 4 hours with 45 g 1,4-dibromo-2-butene, 71 g sodium carbonate and 300 ml dimethylformamide. The mixture is filtered, the filtrate evaporated under reduced pressure, the residue distilled and the fraction boiling at 177°–179°/20 mmHg collected, to yield the 2-(3-chloro-4-pyrrolinophenyl)-propanol, showing in the I.R. spectrum bands at 3368, 1610, 1022, 805 cm$^{-1}$.

In the analogous manner, the following alcohols are prepared (without distillation): 2-(4-pyrrolinophenyl)-propanol, m.p. 91°–94° (diethyl ether); 2-(4-isoindolinophenyl)-propanol, m.p. 189°–192° (diethyl ether); 2-[4-(1-oxoisoindolino)-phenyl]-propanol, m.p. 129°–131° (diethyl ether).

EXAMPLE 41

Preparation of 1,000 capsules each containing 150 mg of the active ingredient:

| Formula: | |
|---|---|
| α-(3-chloro-4-pyrrolino-phenyl)-propionic acid | 150.0 g |
| Microcrystalline cellulose | 170.0 g |
| Hardened, atomized vegetable fat melting at 65–80° | 5.0 g |

PROCEDURE:

All the powders are passed through a screen with openings of 0.6 mm. Then the drug substance is placed in a suitable mixer and mixed first with the fat and then with the cellulose until homogeneous. 325 mg of the mixture are filled into hard gelatine capsules, using a capsule filling machine.

We claim:
1. An anti-inflammatory pharmaceutical composition comprising a. an anti-inflammatory effective amount of a compound of the formula

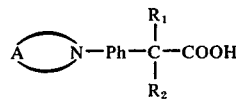

in which $R_1$ is hydrogen, $R_2$ is hydrogen, lower alkyl, 3 to 7 ring-membered cycloalkyl or cycloalkyl-lower alkyl, Ph is 1,3-or 1,4-phenylene, (lower alkyl)-1,3- or 1,4-phenylene, (halogeno)-1,3- or 1,4-phenylene or (trifluoromethyl)-1,3- or 1,4-phenylene and the group A N- is 1-oxo-isoindolino, or a lower alkyl ester, an alkali metal or alkaline earth metal salt, or a therapeutically useful acid addition salt thereof, and (b) a pharmaceutical excipient suitable for enteral, parenteral or topical application.

2. A composition as claimed in claim 1, in which formula of the effective compound $R_1$, Ph and

have the meaning given in claim 1, and $R_2$ is 3 to 7 ring-membered cycloalkyl or cycloalkyl-lower alkyl, or the functional derivatives thereof listed in claim 1.

3. A composition as claimed in claim 1, which effective compound corresponds to the formula

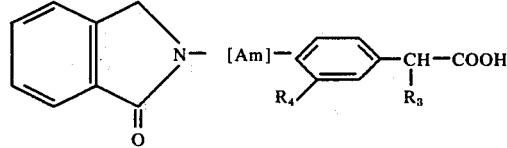

in which $R_3$ is hydrogen or alkyl with up to 4 carbon atoms, $R_4$ is hydrogen, alkyl with up to 4 carbon atoms, halogeno or trifluoromethyl, or the methyl, ethyl, n- or i-propyl or -butyl ester, the sodium or potassium salt or a therapeutically useful acid addition salt thereof.

4. A composition as claimed in claim 2, which effective compound corresponds to the formula

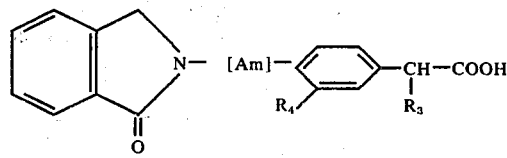

in which $R_3$ is 3 or 4 ring-membered lower cycloalkyl or cycloalkylmethyl, $R_4$ is hydrogen, alkyl with up to 4 carbon atoms, halogeno, trifluoromethyl, or the methyl, ethyl, n- or i-propyl or -butyl ester, the sodium potassium salt or a therapeutically useful acid addition salt thereof.

5. A composition as claimed in claim 3, in which formula of the effective compound $R_3$ is hydrogen or methyl, ethyl, n- or i-propyl, $R_4$ is hydrogen, fluoro, chloro or trifluoromethyl, or the methyl or ethyl ester, the sodium or potassium salt or a therapeutically useful acid addition salt thereof.

6. A composition as claimed in claim 4, in which formula of the effective compound $R_3$ is cyclopropyl or cyclopropylmethyl, $R_4$ is hydrogen, fluoro, chloro or trifluoromethyl, or the methyl or ethyl ester, the sodium or potassium salt or a therapeutically useful acid addition salt thereof.

* * * * *

UNITED STATES PATENT AND TRADEMARK OFFICE
CERTIFICATE OF CORRECTION

PATENT NO. : 3,997,669

DATED : December 14, 1976

INVENTOR(S) : Richard William James Carney et al

It is certified that error appears in the above-identified patent and that said Letters Patent are hereby corrected as shown below:

Column 1, line 9, delete "1972" and substitute --- 1971 ---;
line 18, delete "3,691,040" and substitute --- 3,641,040 ---;
line 42, delete "radial" and substitute --- radical ---.

Column 3, line 22, after "free" delete "of" and substitute -- or ---.

Column 4, line 14, before "saline" insert --- aqueous ---;
line 35, after "treatment" delete "of" and substitute --- or ---
line 38, delete "or" and substitute --- of ---.

Column 5, line 13, delete "akyl ester" and substitute --- alkyl ester ---;   line 33, after "(lower alkyl" insert --- )- ---.

Column 9, line 7, delete "pergenzoic" and substitute --- perbenzoic ---.

Column 11, line 37, delete "of" and substitute --- or ---;
line 60, delete "hdrazono" and substitute --- hydrazono ---.

Column 15, line 41, delete "alkenyl" and substitute --- alkenal ---.

UNITED STATES PATENT OFFICE
CERTIFICATE OF CORRECTION

Patent No. 3,997,669               Dated Dec. 14, 1976

Inventor(s) Richard William James Carney          Page 2 of 2

It is certified that error appears in the above-identified patent and that said Letters Patent are hereby corrected as shown below:

Column 36, lines 14-15, delete "or a therapeutically useful acid addition salt thereof"; in the formula of claim 3, delete "[Am]" and substitute a connecting line; lines 39-40, delete "or a therapeutically useful acid addition salt"; in the formula of claim 4, delete "[Am]" and substitute a connecting line; line 54, after "sodium" insert --- or ---; lines 55-56, delete "or a therapeutically useful acid addition salt"; lines 61-62, delete "or a therapeutically useful acid addition salt"; lines 66-67, delete "or a therapeutically useful acid addition salt".

Signed and Sealed this

Twenty-fourth Day of May 1977

[SEAL]

Attest:

RUTH C. MASON
Attesting Officer

C. MARSHALL DANN
Commissioner of Patents and Trademarks